United States Patent
Taylor et al.

(10) Patent No.: US 10,898,664 B2
(45) Date of Patent: Jan. 26, 2021

(54) VENTILATOR APPARATUS AND METHOD

(71) Applicant: ResMed Paris SAS, Moissy-Cramayel (FR)

(72) Inventors: Kenneth Taylor, Kellyville (AU); Simon Robert Cork, Wollstonecraft (AU); Jonathan Huw Thomas, Lilyfield (AU); Eva Ng, Erskineville (AU); Benjamin John Leavens, Woollahra (AU); Enrico Brambilla, Milan (IT); Frank Van Regteren, Bella Vista (AU); Philippe Auguste Chalvignac, Moissy Cramayel (FR); Zdzislaw Antoni Ziolkowski, Earlwood (AU); Arthur Kin-Wai Yee, Sydney (AU); Geoff Crumblin, Baulkham Hills (AU); David Creusot, Sydney (AU)

(73) Assignee: ResMed Paris SAS

( * ) Notice: Subject to any disclaimer, the term of this patent is extended or adjusted under 35 U.S.C. 154(b) by 933 days.

(21) Appl. No.: 15/485,497

(22) Filed: Apr. 12, 2017

(65) Prior Publication Data
US 2017/0340847 A1    Nov. 30, 2017

Related U.S. Application Data

(60) Division of application No. 13/624,167, filed on Sep. 21, 2012, now Pat. No. 9,649,459, which is a (Continued)

(51) Int. Cl.
*A61M 16/00* (2006.01)
*A61M 16/20* (2006.01)
(Continued)

(52) U.S. Cl.
CPC .... *A61M 16/0066* (2013.01); *A61M 16/0069* (2014.02); *A61M 16/0858* (2014.02);
(Continued)

(58) Field of Classification Search
CPC .............. A61M 16/0816; A61M 16/20; A61M 16/107; A61M 16/125; F04D 9/048; F04D 25/0666
See application file for complete search history.

(56) References Cited

U.S. PATENT DOCUMENTS

| 5,007,420 A | 4/1991 | Bird |
| 5,549,105 A | 8/1996 | Bloch et al. |

(Continued)

FOREIGN PATENT DOCUMENTS

| CA | 2201698 A1 | 10/1998 |
| CN | 101321958 A | 12/2008 |

(Continued)

OTHER PUBLICATIONS

EP Communication enclosing extended EP Search Report issued in corresponding EP application No. 17198437.0 dated Mar. 22, 2018.
(Continued)

*Primary Examiner* — Timothy A Stanis
(74) *Attorney, Agent, or Firm* — Botos Churchill IP Law LLP

(57) ABSTRACT

A respiratory treatment apparatus configured to provide a flow of breathable gas to a patient, including a breathable air outlet, an outside air inlet, and an pneumatic block module, wherein the pneumatic block module includes: a volute assembly including an inlet air passage, a mount for a blower and an outlet air passage; the blower being mounted in the mount such that an impeller of the blower is in a flow passage connecting the inlet air passage and the outlet air passage; a casing enclosing the volute assembly, wherein air
(Continued)

passages within the casing connect air ports on the volute assembly, wherein the inlet air passage of the volute assembly is in fluid communication with the outside air inlet and the outlet air passage of the volute assembly is in fluid communication with the air outlet.

27 Claims, 38 Drawing Sheets

Related U.S. Application Data continuation-in-part of application No. 13/613,958, filed on Sep. 13, 2012, now abandoned.

(60) Provisional application No. 61/539,258, filed on Sep. 26, 2011.

(51) Int. Cl.
  *A61M 16/08* (2006.01)
  *A61M 16/10* (2006.01)
  *A61M 16/12* (2006.01)

(52) U.S. Cl.
  CPC ........ *A61M 16/107* (2014.02); *A61M 16/125* (2014.02); *A61M 16/203* (2014.02); *A61M 16/205* (2014.02); *A61M 2016/0027* (2013.01); *A61M 2016/0042* (2013.01); *A61M 2016/1025* (2013.01); *A61M 2205/128* (2013.01); *A61M 2205/18* (2013.01); *A61M 2205/42* (2013.01); *A61M 2205/502* (2013.01); *A61M 2205/8206* (2013.01)

(56) References Cited

U.S. PATENT DOCUMENTS

| | | | |
|---|---|---|---|
| 5,755,224 A | 5/1998 | Good et al. | |
| 7,975,688 B1 | 7/2011 | Truitt | |
| 2002/0148468 A1* | 10/2002 | Valeij | A61M 16/00 128/202.27 |
| 2005/0039748 A1 | 2/2005 | Andrieux | |
| 2005/0103339 A1 | 5/2005 | Daly et al. | |
| 2005/0103341 A1 | 5/2005 | Deane et al. | |
| 2007/0131228 A1 | 6/2007 | Croll et al. | |
| 2008/0072900 A1 | 3/2008 | Kenyon et al. | |
| 2008/0257346 A1 | 10/2008 | Lathrop et al. | |
| 2008/0310978 A1* | 12/2008 | Hoffman | F04D 29/40 417/420 |
| 2009/0020117 A1 | 1/2009 | Haase et al. | |
| 2009/0071478 A1* | 3/2009 | Kalfon | A61M 16/0858 128/204.17 |
| 2010/0139657 A1* | 6/2010 | Chalvignac | A61M 16/0057 128/204.22 |
| 2010/0170513 A1 | 7/2010 | Bowditch et al. | |
| 2010/0186744 A1 | 7/2010 | Andrieux | |
| 2010/0307490 A1* | 12/2010 | Broborg | A61M 16/009 128/203.12 |
| 2011/0009762 A1 | 1/2011 | Eichler et al. | |
| 2011/0126832 A1 | 6/2011 | Winter | |
| 2011/0197882 A1* | 8/2011 | Truschel | A61M 16/202 128/204.18 |
| 2016/0175554 A1 | 6/2016 | Lithgow et al. | |

FOREIGN PATENT DOCUMENTS

| | | |
|---|---|---|
| DE | 102007005819 B3 | 12/2007 |
| EP | 0266964 A2 | 5/1988 |
| EP | 1238681 A1 | 9/2002 |
| FR | 2953142 A1 | 6/2011 |
| JP | H11508159 A | 7/1999 |
| JP | 2002315830 A | 10/2002 |
| JP | 2008518640 A | 6/2008 |
| JP | 2009518583 A | 5/2009 |
| JP | 2009519058 A | 5/2009 |
| JP | 2011030990 A | 2/2011 |
| WO | 9700092 A1 | 1/1997 |
| WO | 9922794 A1 | 5/1999 |
| WO | 9947197 A1 | 9/1999 |
| WO | 03047671 A1 | 6/2003 |
| WO | 2007068132 A1 | 6/2007 |
| WO | 2007070308 A1 | 6/2007 |
| WO | 2009062547 A1 | 5/2009 |
| WO | 2010028121 A1 | 3/2010 |
| WO | 2010044037 A2 | 4/2010 |
| WO | 2011051462 A2 | 5/2011 |

OTHER PUBLICATIONS

JP Decision of Rejection to JP Application No. 2017-075817.
Office Action issued in corresponding JP application No. 2017-075817 dated Mar. 16, 2018.
Examination Decision on Request for Reexamination issued in corresponding CN application No. 201210363250.2 dated Dec. 5, 2017.

* cited by examiner

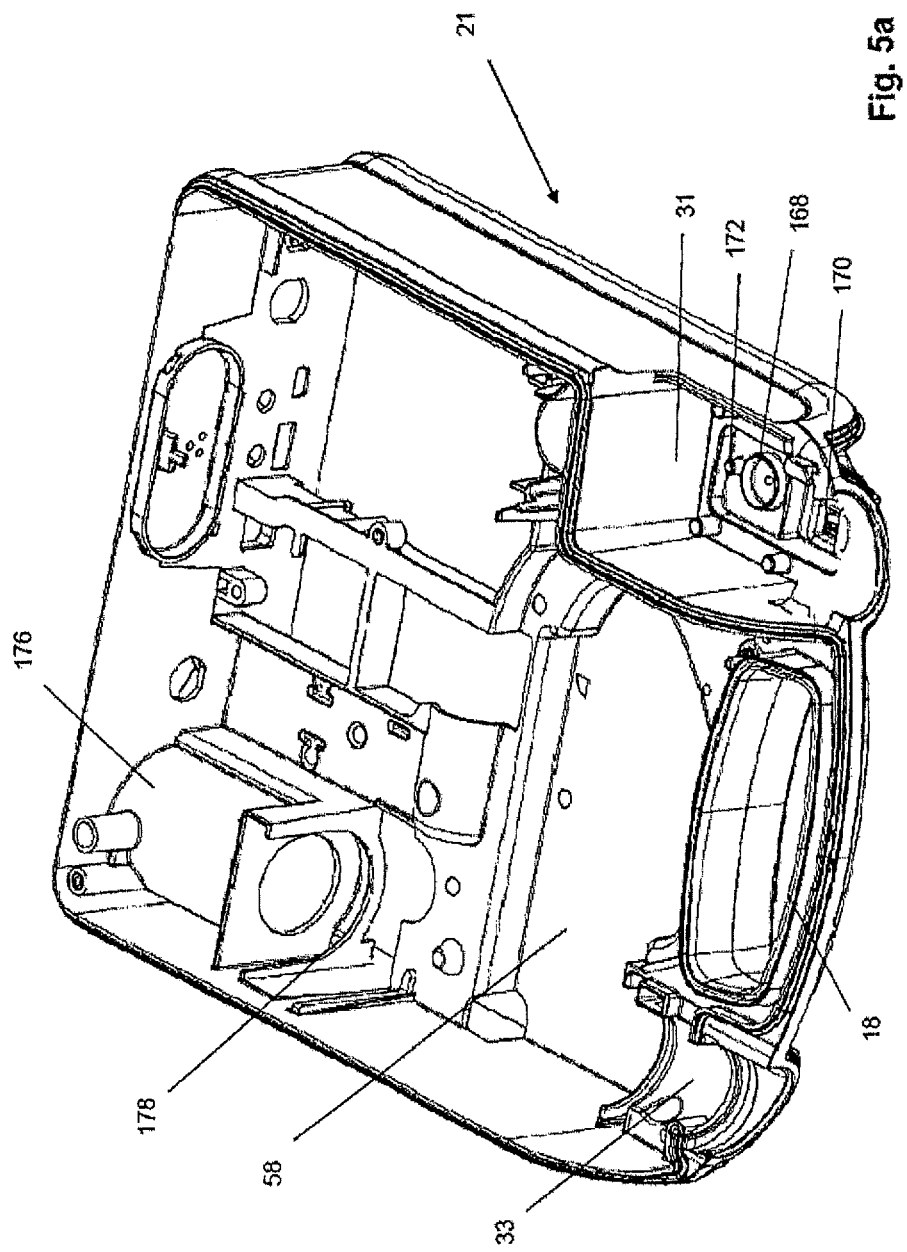

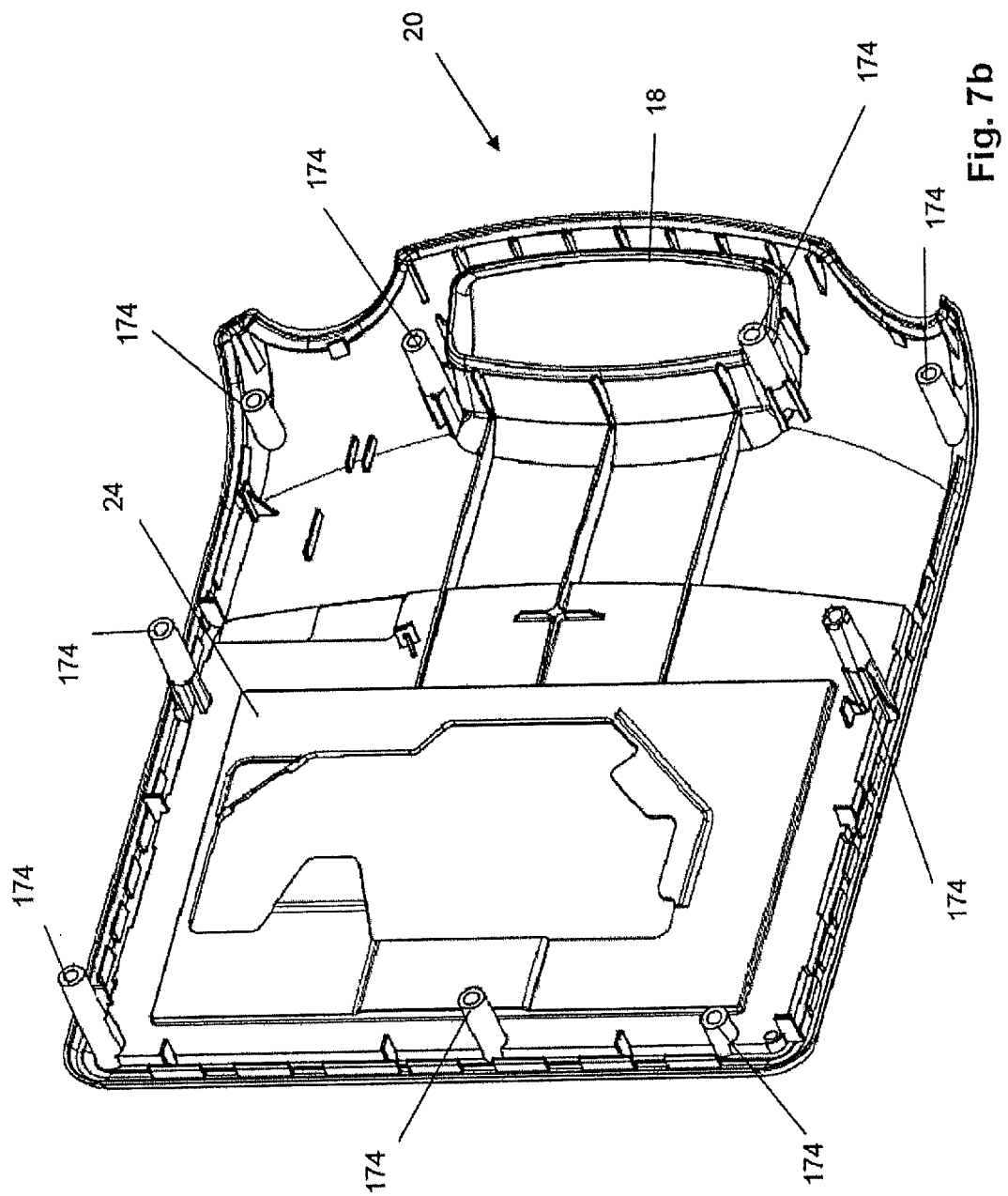

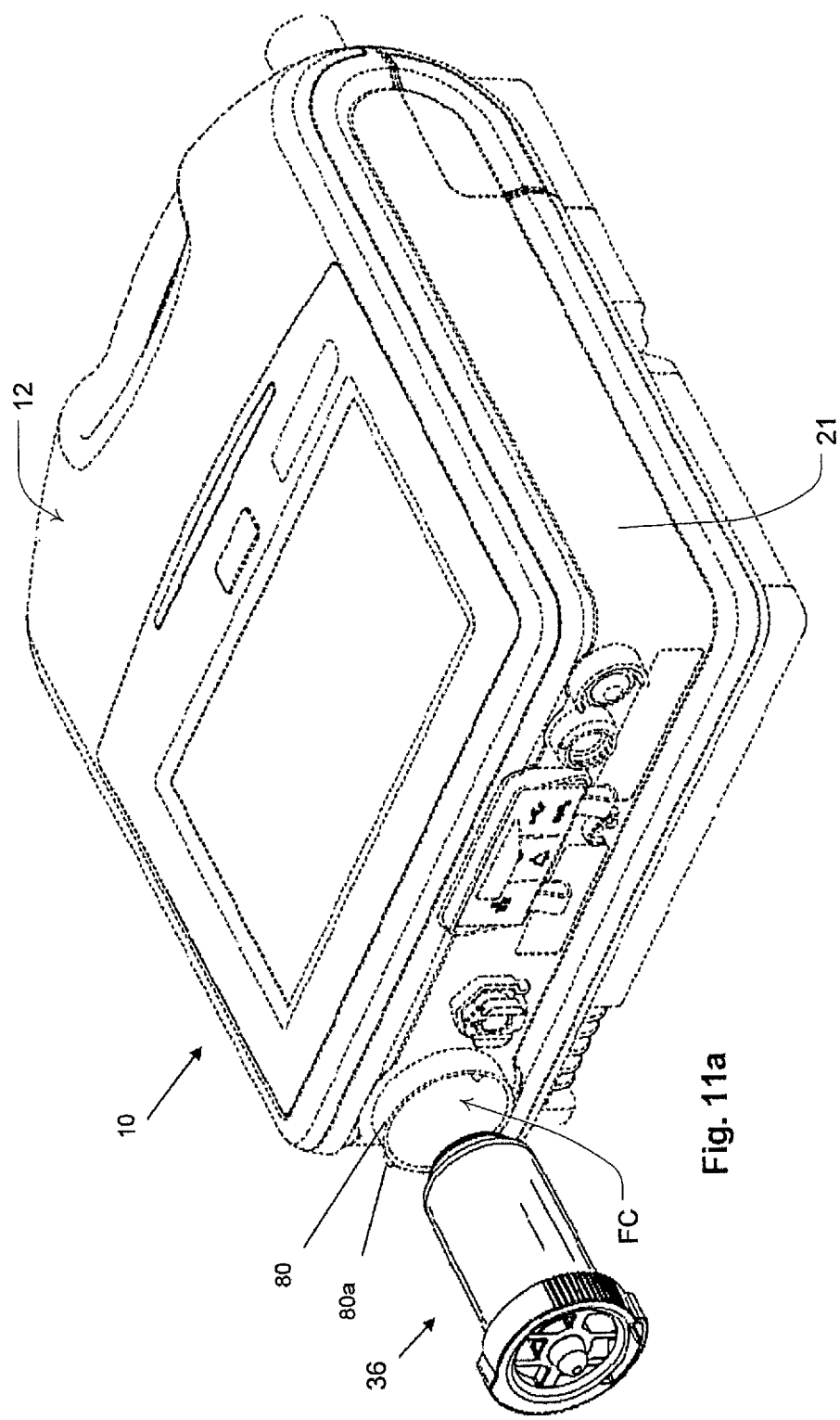

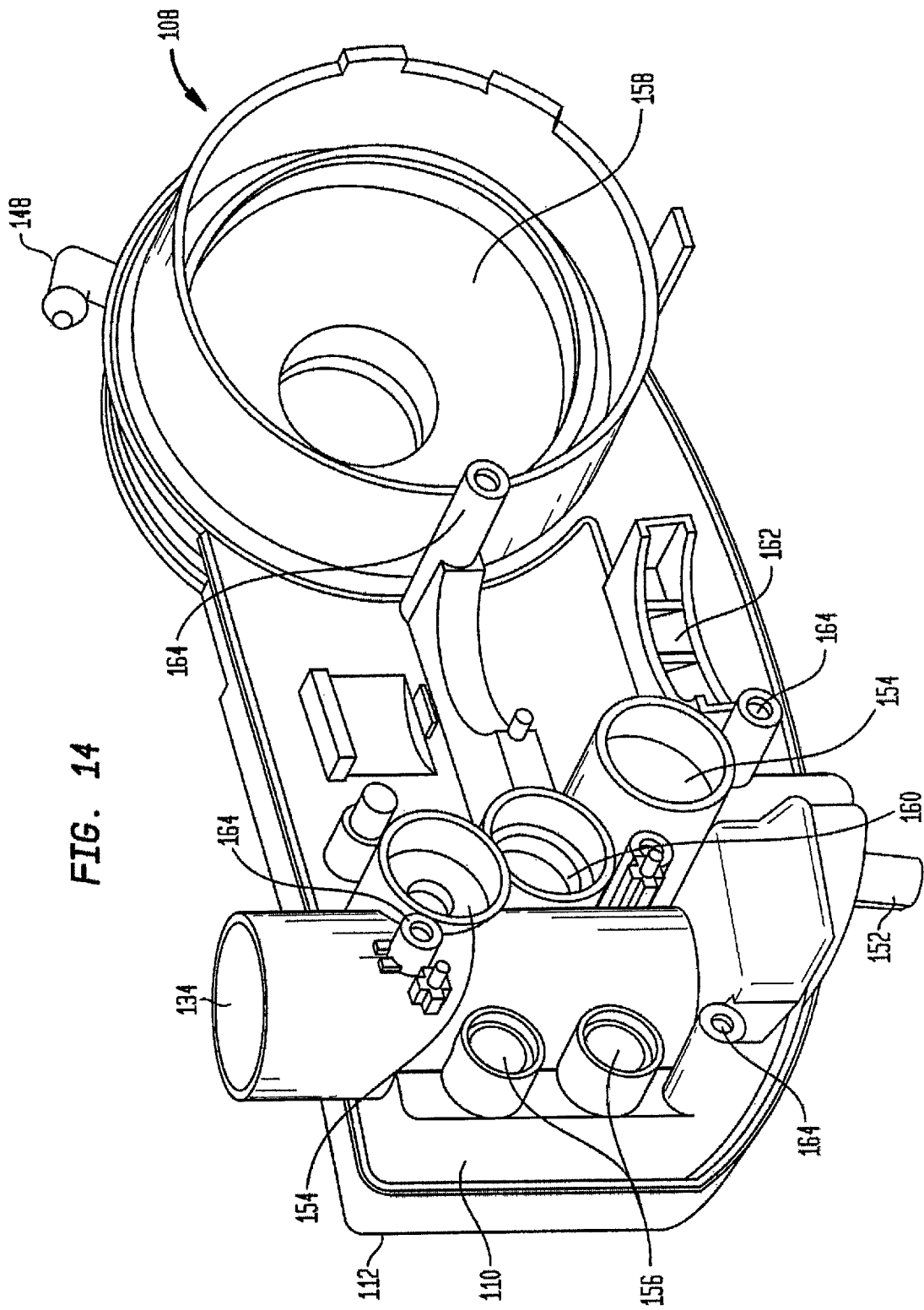

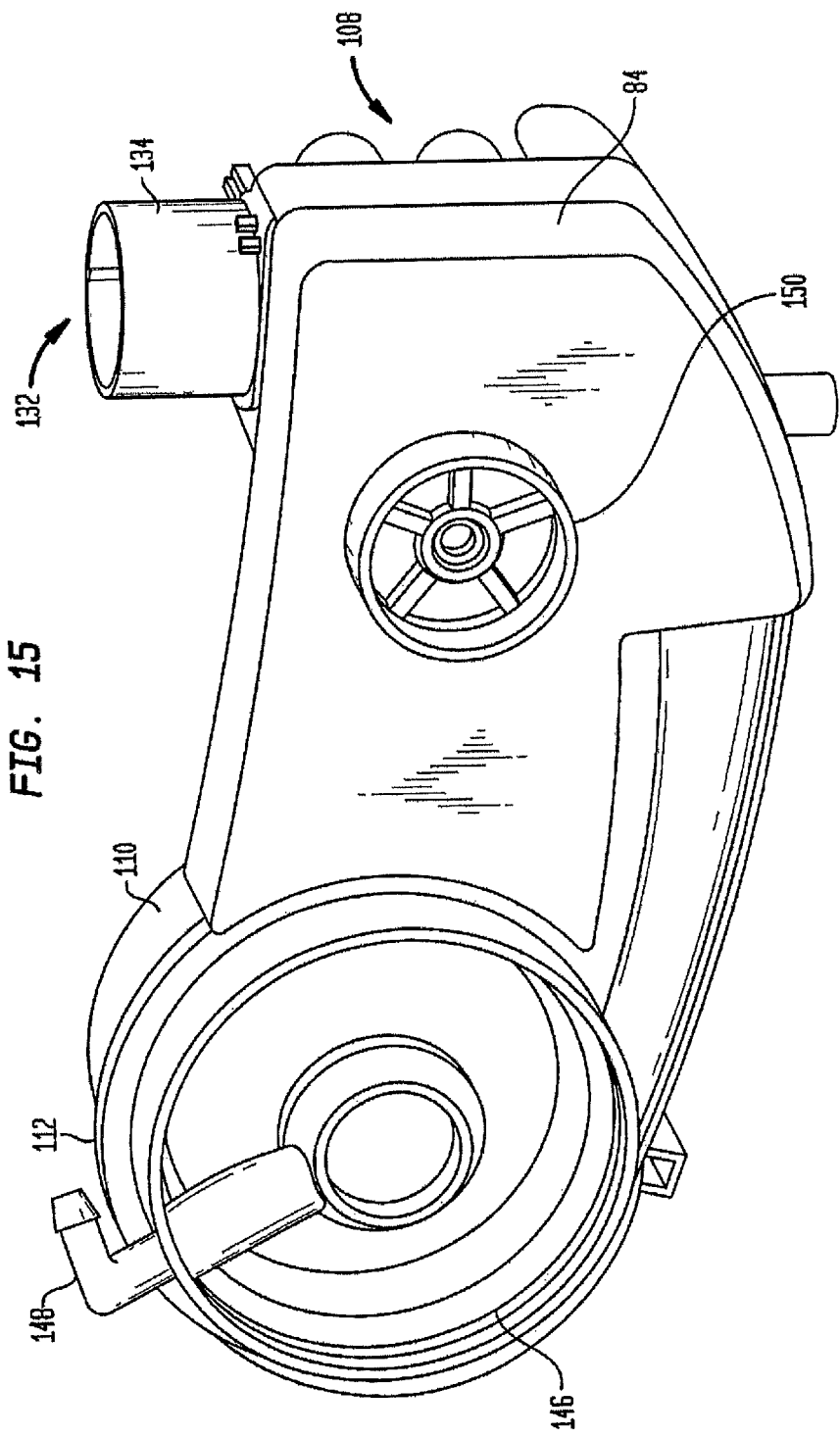

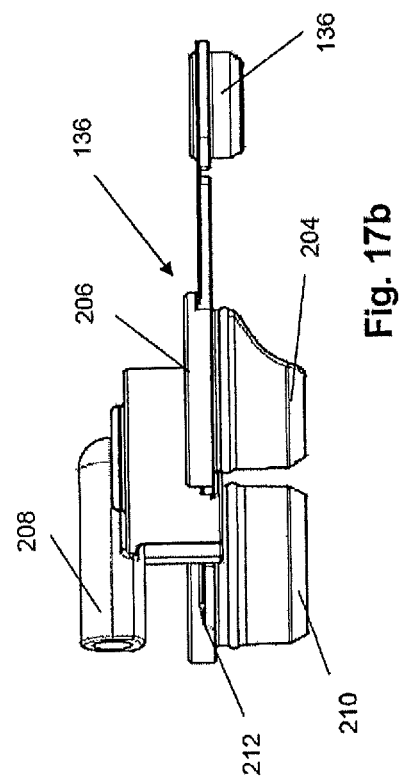
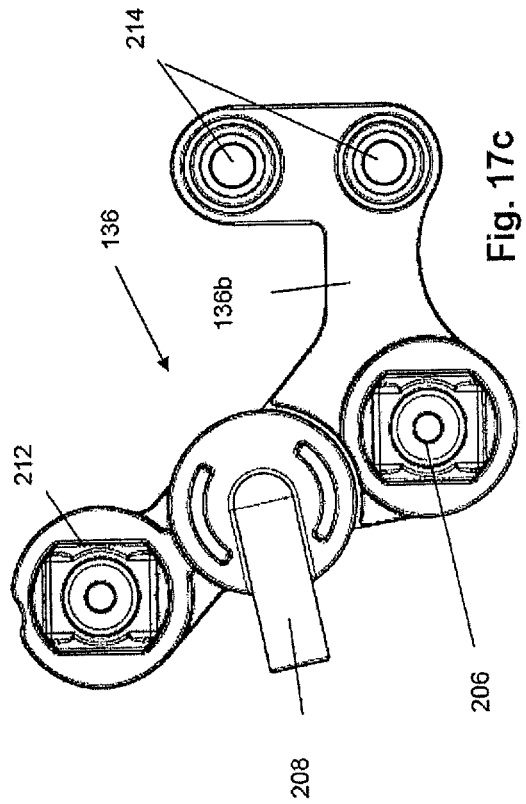
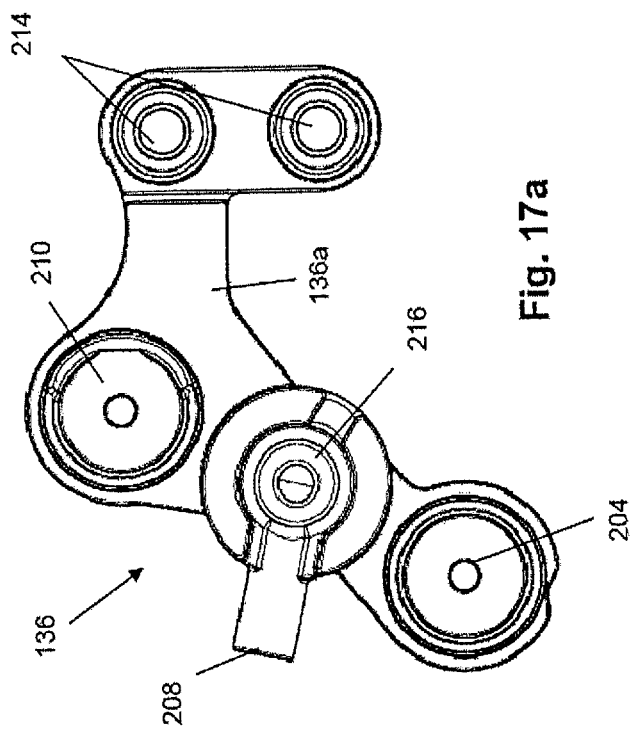
Fig. 17b
Fig. 17c
Fig. 17a

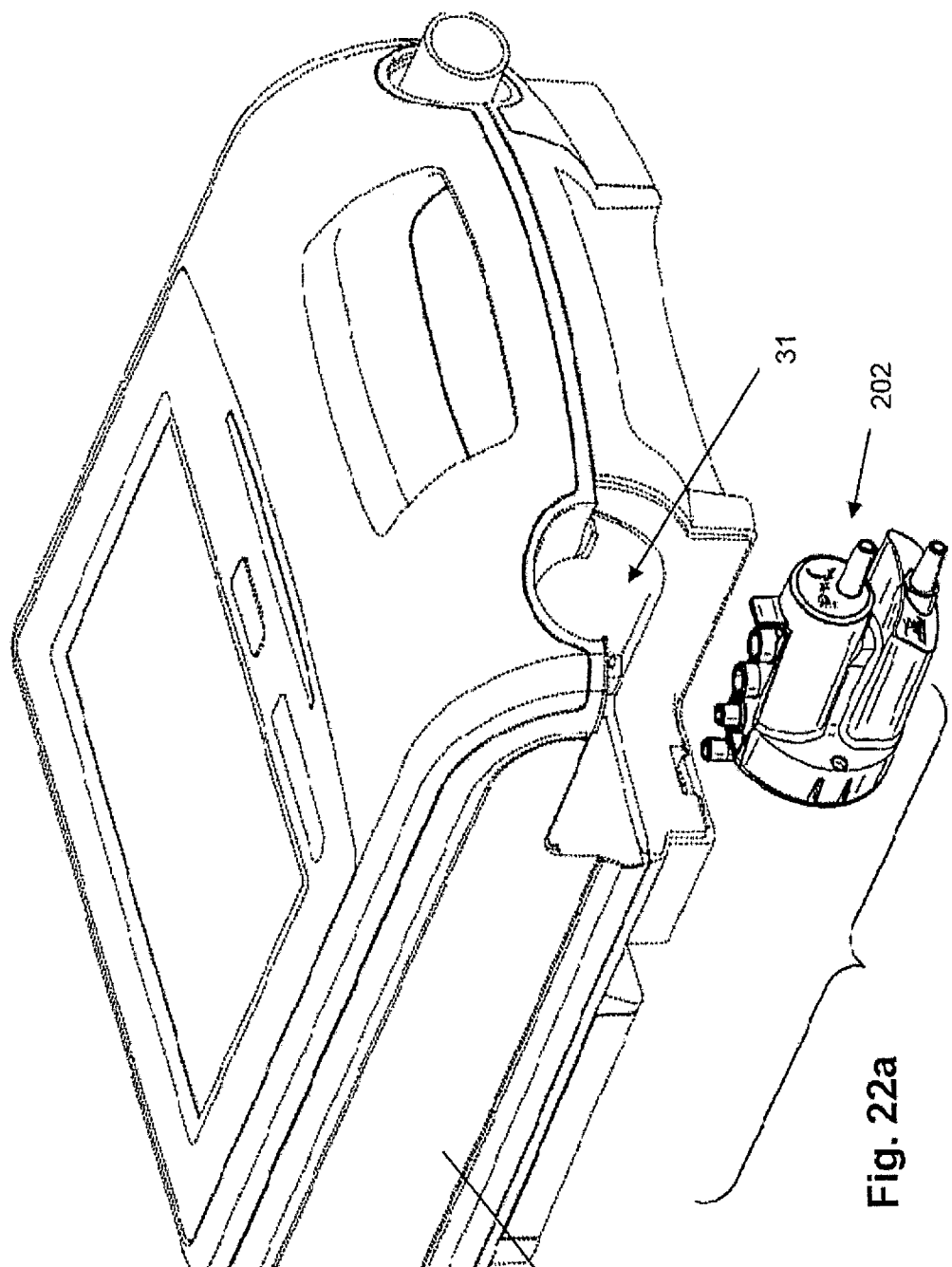

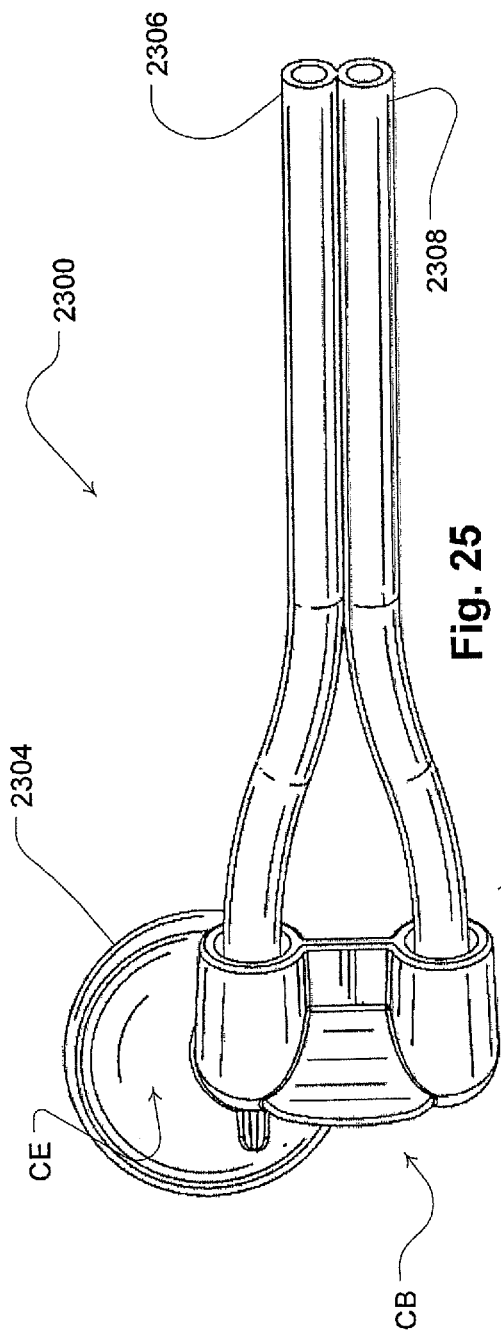
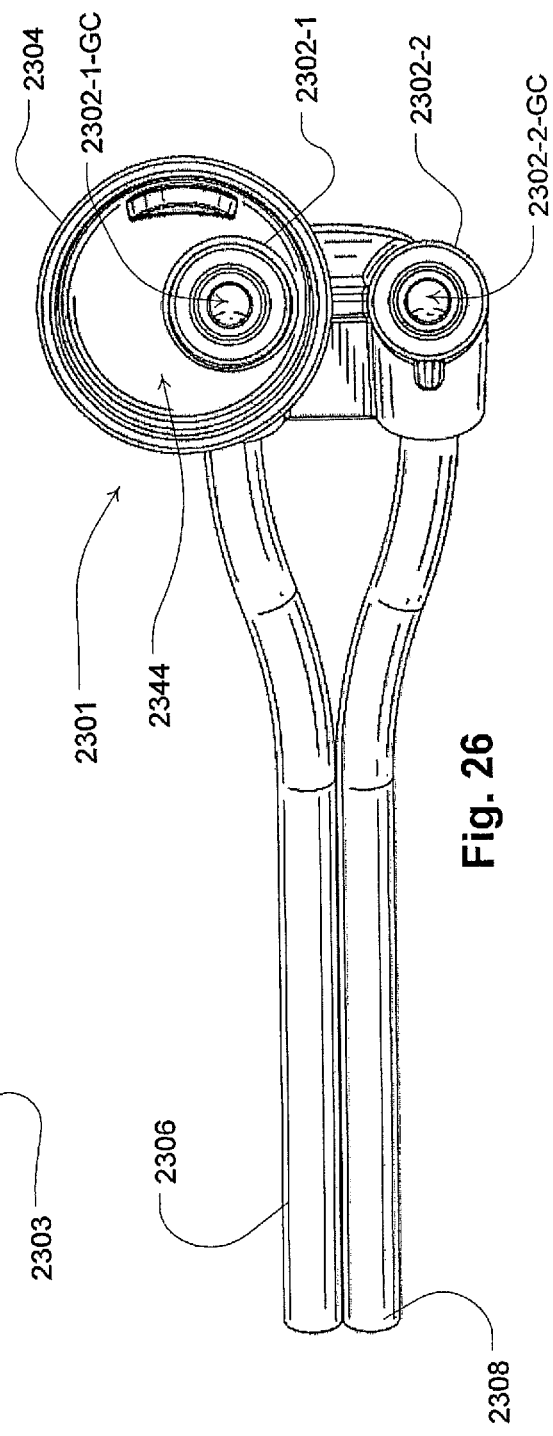

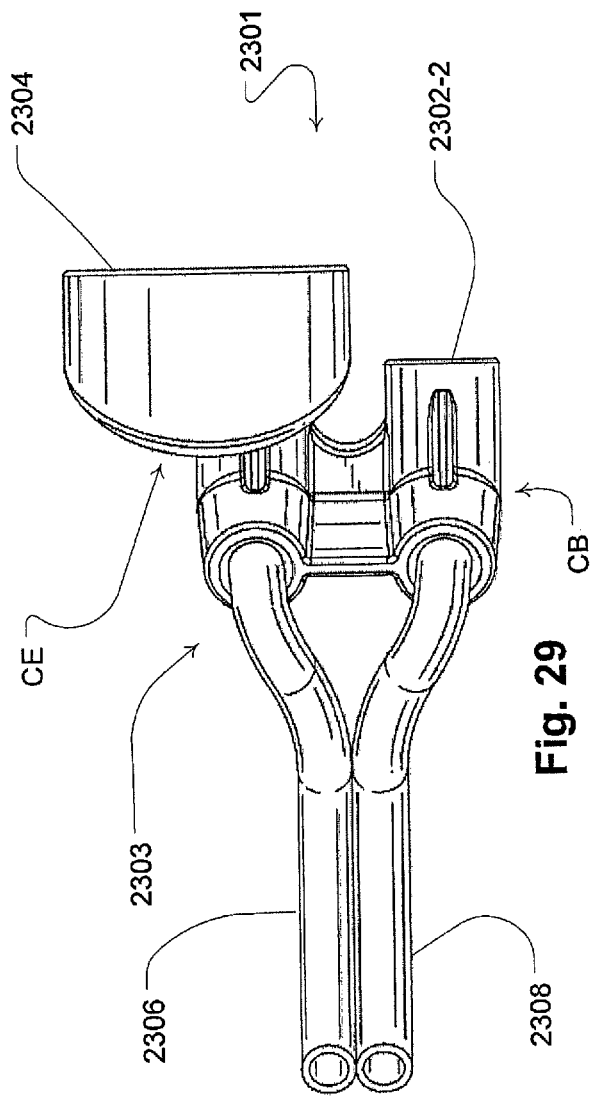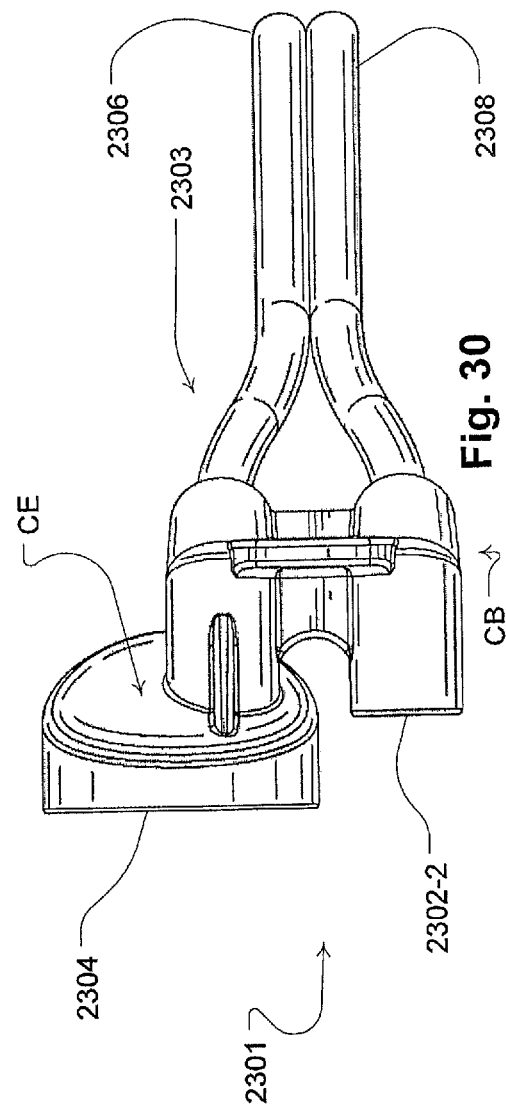

VENTILATOR APPARATUS AND METHOD

CROSS REFERENCE TO RELATED APPLICATIONS

This application is a divisional of U.S. application Ser. No. 13/624,167 which is a continuation-in-part of U.S. application Ser. No. 13/613,958, filed on Sep. 13, 2012, which claims the benefit of the filing date of U.S. Provisional Patent Application No. 61/539,258 filed Sep. 26, 2011, the disclosures of which are incorporated herein by reference.

FIELD OF THE TECHNOLOGY

The present technology relates to ventilators and other respiratory treatment devices that provide breathing assistance to patients.

BACKGROUND OF THE TECHNOLOGY

Ventilators help patients to breath by mechanically pumping and exhausting air from the lungs. Ventilators may be used to replace or supplement the patient's muscular effort normally used to inflate and deflate the lungs.

Ventilators may function to supply a patient with a supply of clean breathable gas (usually air, with or without supplemental oxygen) at a therapeutic pressure or pressures, at appropriate times during the subject's breathing cycle. Pressure changes may be implemented in a synchronized fashion so as to permit greater pressures during inspiration and lower pressures during expiration. Therapeutic pressure is also known as the ventilation pressure.

Ventilators typically include a flow generator, an inlet filter, a mask, an air delivery conduit connecting the flow generator to the mask, various sensors and a microprocessor-based controller. Optionally, in lieu of a mask, a tracheotomy tube may also serve as a patient interface. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

Ventilators also control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

Ventilators provide breathing assistance to patient suffering from diseases affecting the musculature required for breathing, such as muscular dystrophies, polio, amyotrophic lateral sclerosis (ALS), and Guillain-Barre syndrome. Ventilators may be used to treat conditions such as respiratory insufficiency or failure due to lung, neuromuscular or musculoskeletal disease and diseases of respiratory control. They may also be used for conditions related to sleep disordered breathing (SDB) (including mild obstructive sleep apnea (OSA)), allergy induced upper airway obstruction or early viral infection of the upper airway. Ventilators are also used to provide breathing assistance to sedated patients undergoing surgery or for patients suffering severe injuries, such as high spinal cord injuries and head traumas. In addition, a ventilator may also be configured to expand non-functioning regions of a patient's lung(s), such as collapsed alveoli.

Ventilators conventionally are mechanically complex devices which require highly trained persons to service and repair. Within the housing of a ventilator are a number of various tubes to connect mechanical and electrical valves and sensors used to control and measure the characteristics of ventilation. The tubes are typically individually connected to various ports and devices in the housing of the ventilator.

BRIEF SUMMARY OF THE TECHNOLOGY

An aspect of some embodiments of the current technology is to provide an apparatus for a ventilator or other respiratory treatment apparatus, collectively referred to herein as ventilators. Another aspect of some embodiments of the technology is to provide less mechanically complex ventilator. A further aspect of certain embodiments of the technology is a pneumatic block module which consolidates air passages within a ventilator. The pneumatic block module may include a volute assembly including a blower and air passages for the ventilator.

The current technology may be embodied as a respiratory treatment apparatus configured to provide a flow of breathable gas to a patient, including a breathable air outlet, an outside air inlet, and a pneumatic block module, wherein the pneumatic block module comprises: a volute assembly including an inlet air passage, a mount for a blower and an outlet air passage; the blower being mounted in the mount such that an impeller of the blower is in a flow passage connecting the inlet air passage and the outlet air passage; a casing enclosing the volute assembly, wherein air passages within the casing connect air ports on the volute assembly, wherein the inlet air passage of the volute assembly is in fluid communication with the outside air inlet and the outlet air passage of the volute assembly is in fluid communication with the air outlet. The respiratory treatment apparatus may be a ventilator.

The volute assembly may be a molded rigid plastic device and the casing may be metallic having a lower portion and top cover. The casing may have an air passage between the outside air inlet and the inlet air passage of the volute. The air passage in the casing may be formed between a bottom plate of the casing and a cover for the bottom plate.

A removable inlet filter assembly may be aligned with the outside air inlet, wherein the removable inlet filter assembly is held in a casing including the air inlet, and the casing and inlet filter assembly are removable from the housing.

A deformable connector may be sandwiched between the volute assembly and a printed circuit board, wherein pressure sensors on the printed circuit board align with ports through the connector when the printed circuit board seats on the volute assembly and the ports on the connector are open to air passages in the volute assembly.

Some embodiments of the present technology may involve a coupler for a gas routing module of a respiratory treatment apparatus. The coupler may include a coupler body with a plurality of pneumatic channels. The coupler may also include first and second port connectors. The first and second port connectors may be configured on the coupler body for connection to a respiratory treatment apparatus at a ventilator connection end of the coupler body. The coupler may also include first and second conduits. The first and second conduits may be integrated with the coupler body and may be configured as pneumatic channels linked to the first and second port connectors respectively. The coupler may further include an alignment protuberant of the coupler body. The alignment protuberant may be configured to limit orientation of the first and second port connectors to only one connection configuration with the respiratory treatment apparatus.

In some cases, the alignment protuberant may include a connection ring for insertion within a housing channel of the respiratory treatment apparatus. The alignment protuberant may include a cylindrical chamber. The first port connector may be formed in an offset position within an interior portion of the cylindrical chamber. The second port connector may be formed in an exterior portion of the cylindrical chamber. Optionally, the first port connector may include a gas channel for an expiratory pressure from a respiratory mask. The second port connector may include a PEEP control gas channel for a proximal valve. In some cases, the connection ring of the alignment protuberant may include a chamfered cylinder. A surface of the chamfered cylinder may be configured for alignment with an exterior housing surface of the respiratory treatment apparatus. Optionally, the coupler body may include a bend to angle a direction of the pneumatic channels of the coupler.

Some embodiments of the technology may involve a method for maintaining operation of a ventilator. The method may include removing a pneumatic block from a compartment of a ventilator housing. The ventilator may be located in a patient environment. The pneumatic block may include any one or more of a casing, a volute assembly, a blower and air passages, sensors and/or an integrated calibration record. The method may further include inserting a pneumatic block into the compartment of the ventilator housing, and testing operation of the ventilator in the patient environment.

In some cases, the inserting may include returning the removed pneumatic block to the ventilator housing for operation of the ventilator after servicing. The testing operation of the ventilator may be with the returned pneumatic block. Optionally, the method may include substituting a second pneumatic block in the ventilator housing for the removed pneumatic block. The testing operation of the ventilator may be with the second pneumatic block.

In some cases, the method may include servicing the removed pneumatic block for reuse. The servicing the removed pneumatic block may include cleaning the pneumatic block. The servicing the removed pneumatic block may include calibrating operation of one or more components of the pneumatic block, such as storing calibration data in calibration record of the block. The servicing may be performed in the patient environment. The servicing may be performed away from the patient environment contemporaneously with the ventilator being operable in the patient environment. In some cases, the method may include pre-calibrating the inserted pneumatic block prior to the inserting.

Some examples of the technology may include a pneumatic block apparatus for removable insertion within a ventilator housing. The pneumatic block apparatus may include a casing including air passages; a volute assembly; and a blower coupled with the volute assembly. The casing may enclose the volute assembly. The air passages of the casing may connect air ports on the volute assembly. The pneumatic block apparatus may also include an integrated calibration record.

Further embodiments and features of the present technology will be apparent from the following detailed disclosure, abstract, drawings and the claims.

BRIEF DESCRIPTION OF THE DRAWINGS

Examples of the technology will now be described with reference to the accompanying drawings, in which:

FIGS. 5a and 5b are top and bottom views of a chassis according to an example of the disclosed technology;

FIGS. 7a and 7b are top and bottom views of an upper housing according to an example of the disclosed technology

FIGS. 11a and 11b are illustrations indicating insertion of the filter assembly according to FIGS. 9a to 9c into a ventilator housing according to an example of the disclosed technology;

FIGS. 14 and 15 are top and bottom view of the volute assembly;

FIGS. 17a to 17c are bottom, side and top views of a sensor seal according to an example of the disclosed technology;

FIGS. 22a to 22c indicate how the expiratory adaptor of FIGS. 21a to 21d may be coupled to a ventilator according to an example of the disclosed technology;

FIGS. 25 and 26 are top and bottom views respectively of the coupler of FIG. 23;

FIGS. 29 and 30 are oblique top and oblique bottom views respectively of the coupler of FIG. 23.

DETAILED DESCRIPTION

Ventilator Housing —12

Figure 1:
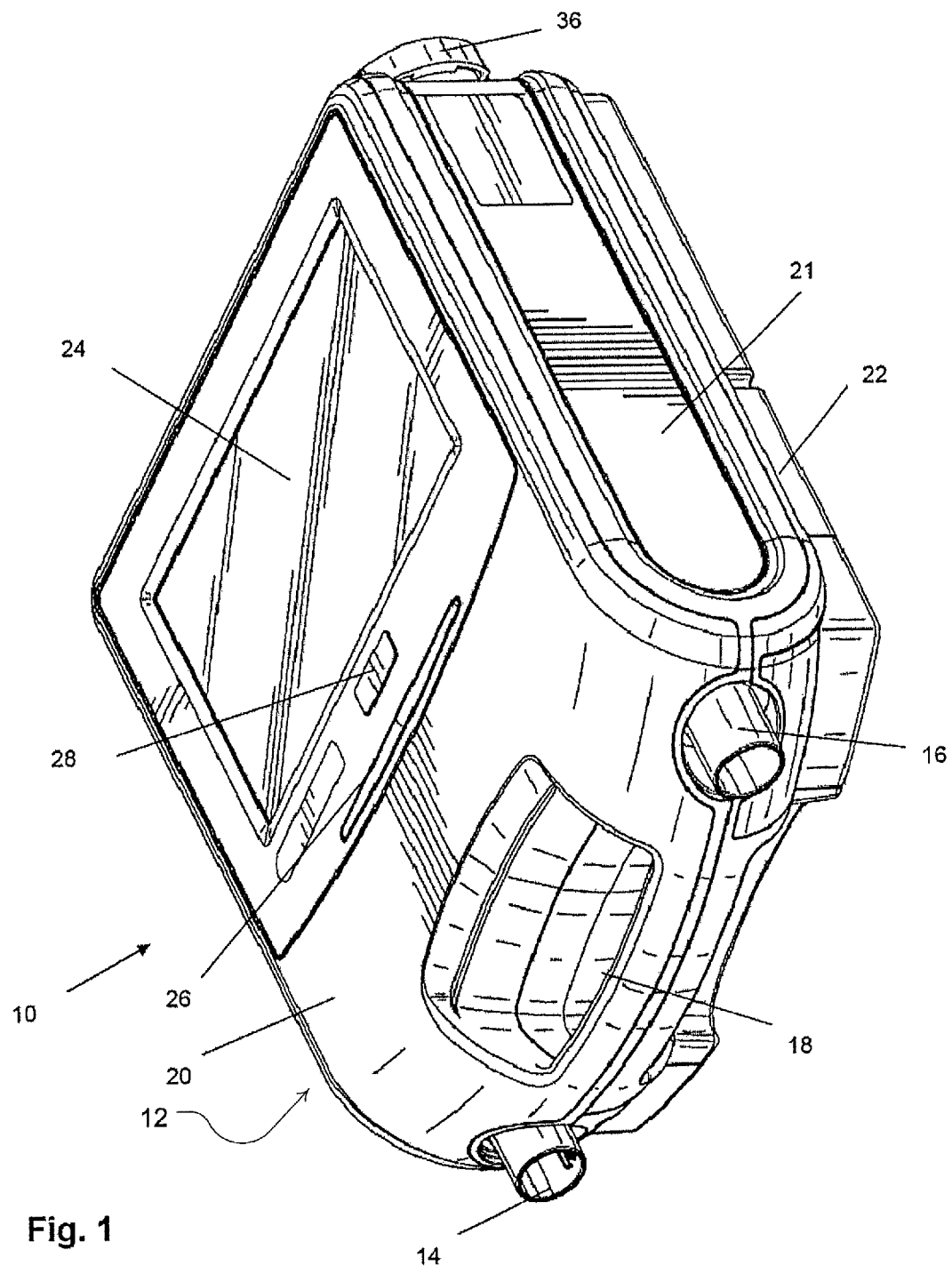
FIG. 1 is a perspective view of a ventilator apparatus according to an example of the disclosed technology.

FIGS. 1 to 4 show a ventilator 10 including a housing 12, an expiration air inlet port 14 and an inspiration outlet port 16. The ports 14 and 16 are connectable to tubes (not shown) which may be inserted into the trachea of a patient, to a face or nasal mask that fits over the nose or mouth or both of a patient, or otherwise attaches to the patient to assist with breathing. The housing for the ventilator may be portable and include a handle 18 for carrying the ventilator. The housing may have an upper housing case 20, a chassis 21 and a lower housing case 22 that are coupled together to form the external faces of the ventilator. However, it is to be understood that the housing may have other configurations such as only comprising two component parts with an upper and lower casing or may have more than three component parts.

Figure 5B:
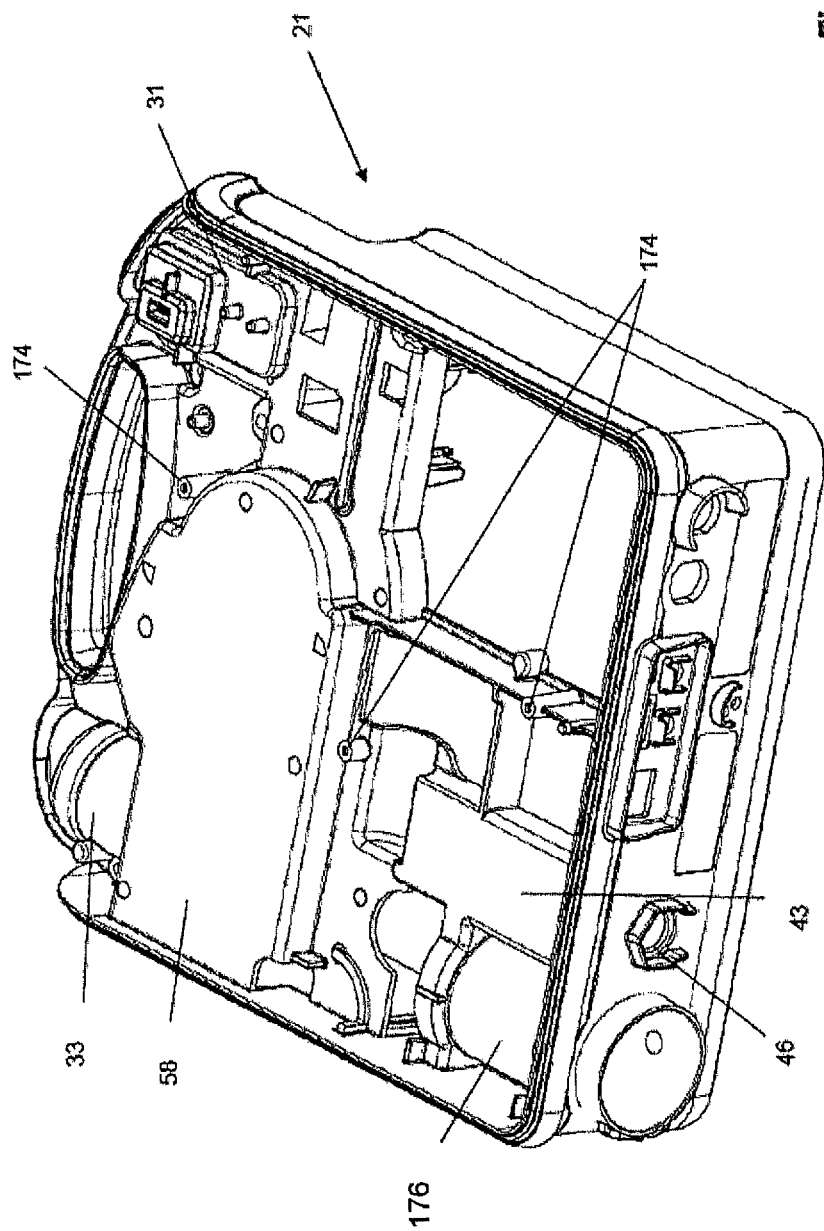

The chassis 21 as seen in FIGS. 5a and 5b may provide the structural skeleton for the ventilator assembly. The chassis 21 may include an inlet filter support 176 and inlet seal support 178 which are adapted to receive an inlet filter assembly 36 and inlet seal 38 respectively described in more detail below. The inlet seal 38 is also configured to couple to an inlet to a pneumatic block module 56. Preferably the inlet seal 38 is formed of a compliant material such as silicone, the inlet seal may be over moulded onto the inlet of the pneumatic block module 56.

The chassis 21 may also comprise a pneumatic block seat into which the pneumatic block module 56 is located for ease of alignment and assembly of the pneumatic block module 56 within the housing. The chassis 21 also may include a portion of the handle 18.

The rear of the chassis 21 may include a range of interfaces for a variety of connections and switches on the rear panel. For example, interfaces for electrical connectors, switches, data connections and oxygen connections.

The chassis 21 also provides a number of interfaces to locate and retain components of the ventilator 10 such as a cooling fan 68, PCB 86, and components of an expiratory portion 31. For example, the expiratory portion 31 of the chassis 21 comprises a positive end expiratory pressure (PEEP) supply port 172, a sensor filter interface 168 and an expiratory flow sensor interface 170 as seen in FIG. 5a. The PEEP supply port 172 may be connected via a tube to a port of a PEEP electrovalve 140 to provide a pneumatic connection from a PEEP blower 124 to an expiratory interface module 200 as required to control the PEEP during expiration. A replaceable sensor filter may be inserted into the sensor filter interface 168 to protect sensors located on the main PCB from contamination from the expired gas. An expiratory flow sensor may be located within the expiratory flow sensor interface 170 (shown in FIG. 5a) to measure the flow rate of the expired gas. The expiratory portion 31 is configured to receive an expiratory seal 70 that is adapted to retain and seal the expiratory sensor filter, expiratory flow sensor and provide a connection to the PEEP supply port 172 as described in more detail below.

The expiratory portion 31 of the ventilator 10 is configured to allow the insertion of an expiratory interface module to receive the expired gas from the patient, such as the expiration air inlet port 14. The different expiratory interface modules include an expiratory valve 200 and an expiratory adaptor 202 (see FIGS. 19a-19d and 21a-21d respectively).

Figure 6A:
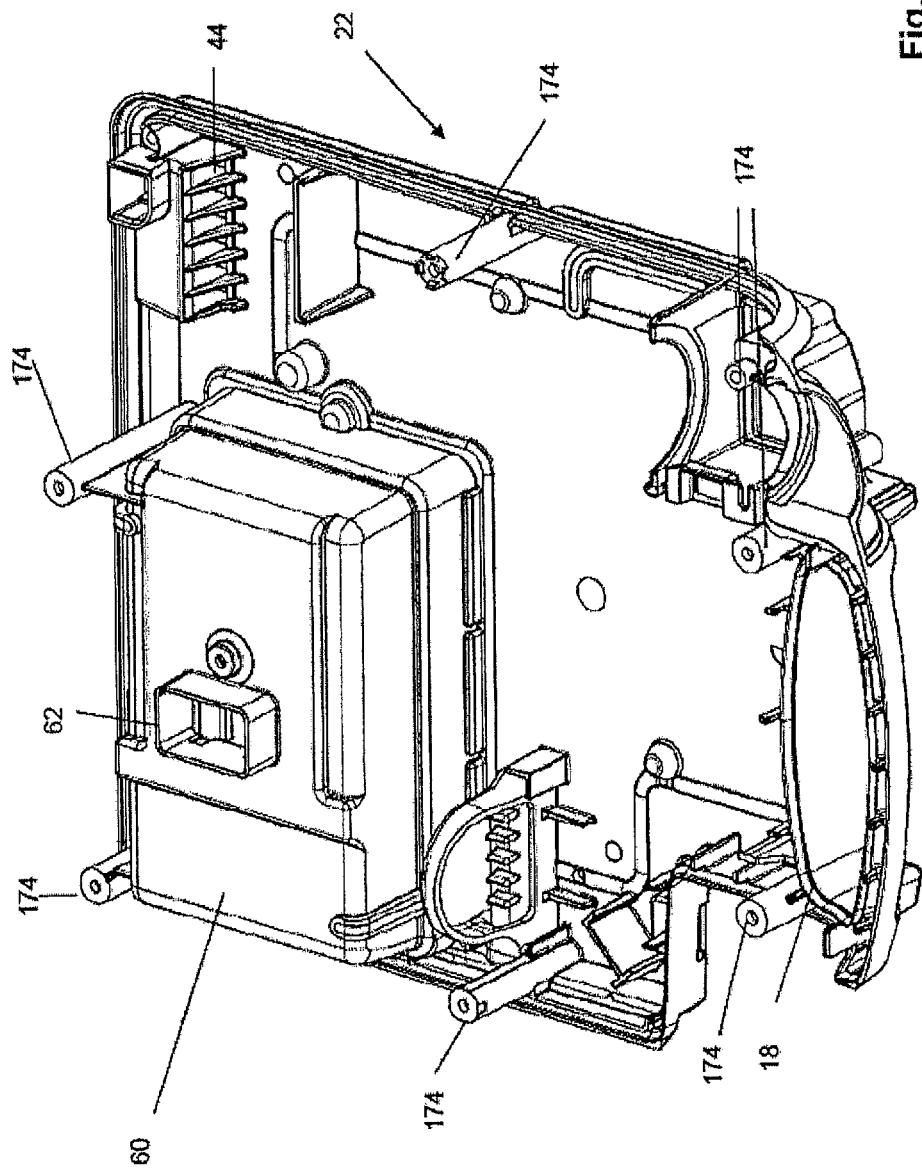
FIGS. 6a and 6b are top and bottom views of a lower housing according to an example of the disclosed technology.
Figure 6B:
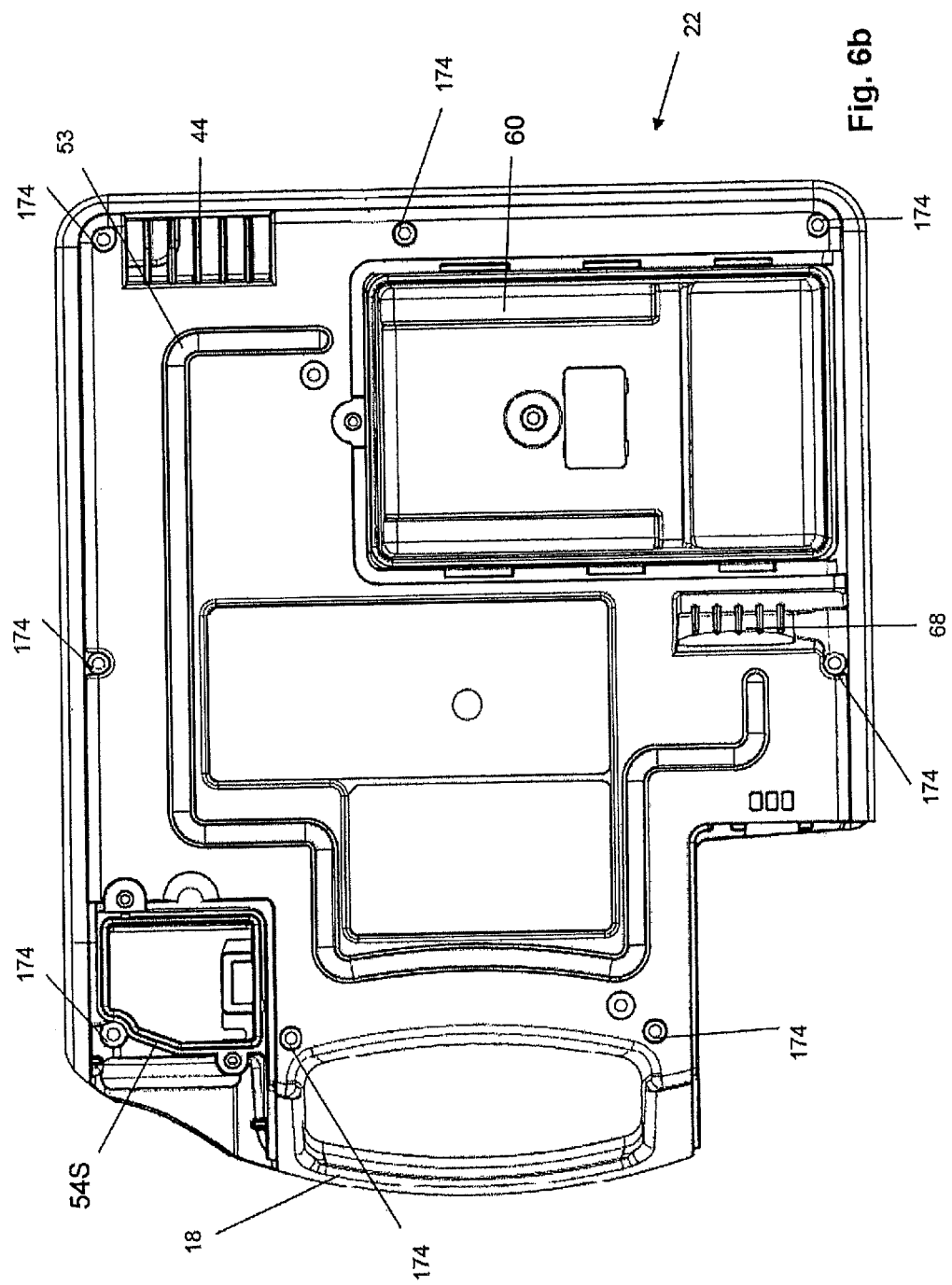

As seen in FIGS. 6a and 6b, the lower housing case 22 includes a battery compartment 60 to locate and interface with a removable battery (not shown) and to provide the battery connector interface 62. A removable battery cover 52 is provided on the outer bottom surface to allow access to insert or remove the battery. A removable expiratory cover 48, an oxygen sensor cover seat 54S to receive an oxygen sensor cover 54 (shown in FIG. 5a) and grills 44 to allow component heat venting are also provided on the outer bottom surface as described in relation to FIG. 4 below. The lower housing may also include an anti-slip foot or grip surface or one or more anti-slip or grip feet 53, such as a thermoplastic polyurethane (TPU) foot, on the outer bottom surface to prevent the ventilator 10 from slipping off a smooth surface. The anti-slip or grip feet 53 may also raise the ventilator 10 to prevent spilt water from pooling under the bottom of the ventilator. A portion of the handle 18 is also located within the lower housing case 22.

Figure 7A:
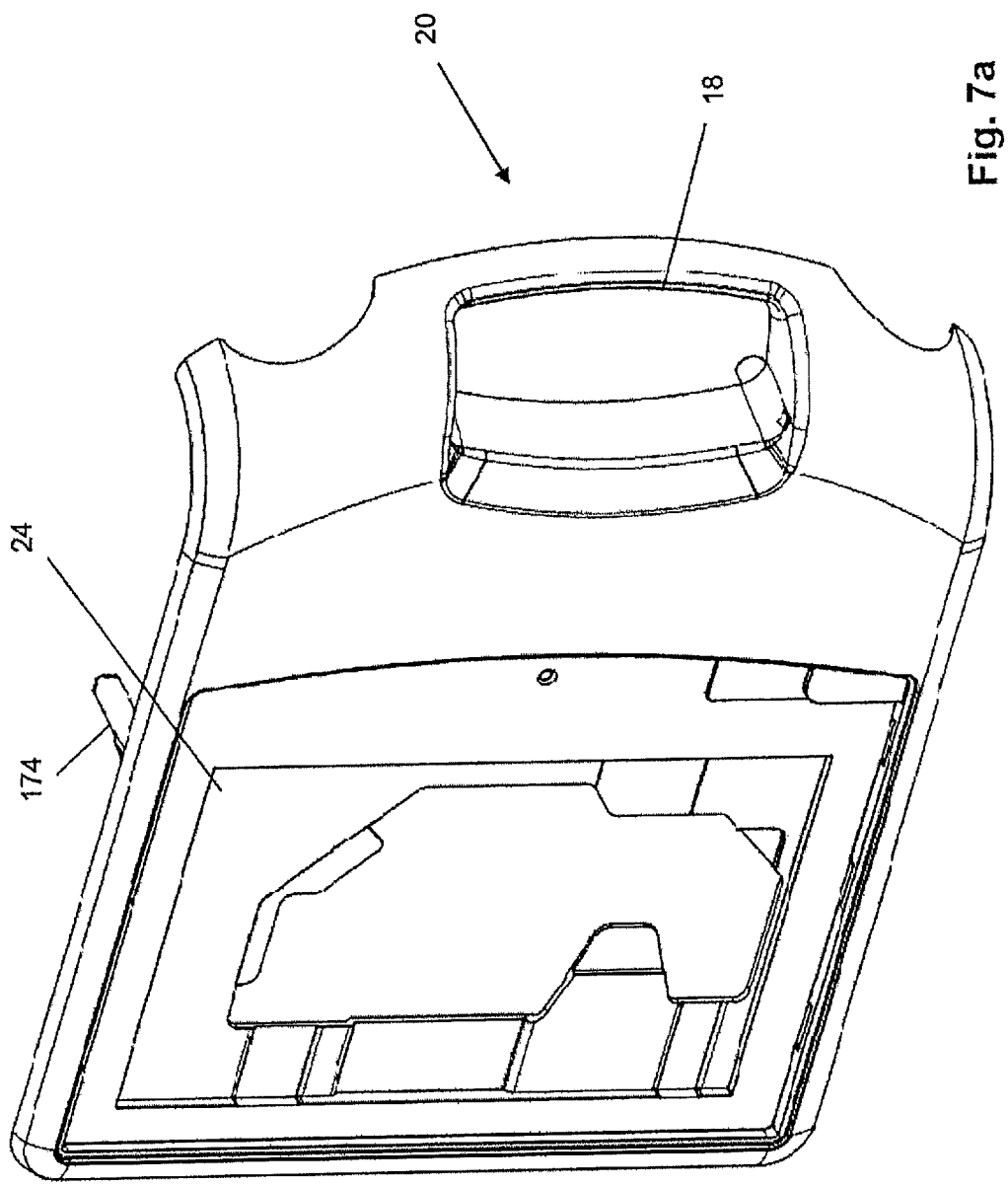

As seen in FIGS. 7a and 7b the upper housing case 20 provides the top face of the ventilator 10 and an interface to receive a user interface display device 24. As shown in FIG. 1, the housing may include a computer or processor driven user interface display device 24, such as a liquid crystal display (LCD) adapted to receive touch inputs for the computer. The display device may be flush with a top surface of the housing to be easily visible while the ventilator is in use. An alarm indicator light bar 26, such as a light emitting diode (LED) light bar, and a button 28 for disabling an audio or visual alarm may be adjacent the display. However it is to be understood that other known user interface systems may be used such as screens, buttons, dial, keys or combinations thereof. The chassis 21, lower housing case 22 and upper housing case 20 may comprise a plurality of screw bosses 174 that may be coupled together for assembly of the complete ventilator housing 12. The chassis 21 is assembled between the upper housing case 20 and the lower housing case 22. The screw bosses 174 may be configured to facilitate ease of assembly by having screw bosses 174 of differing lengths that are configured to couple to specific complementary screw bosses 174 on one of the other housing components.

Figure 2:
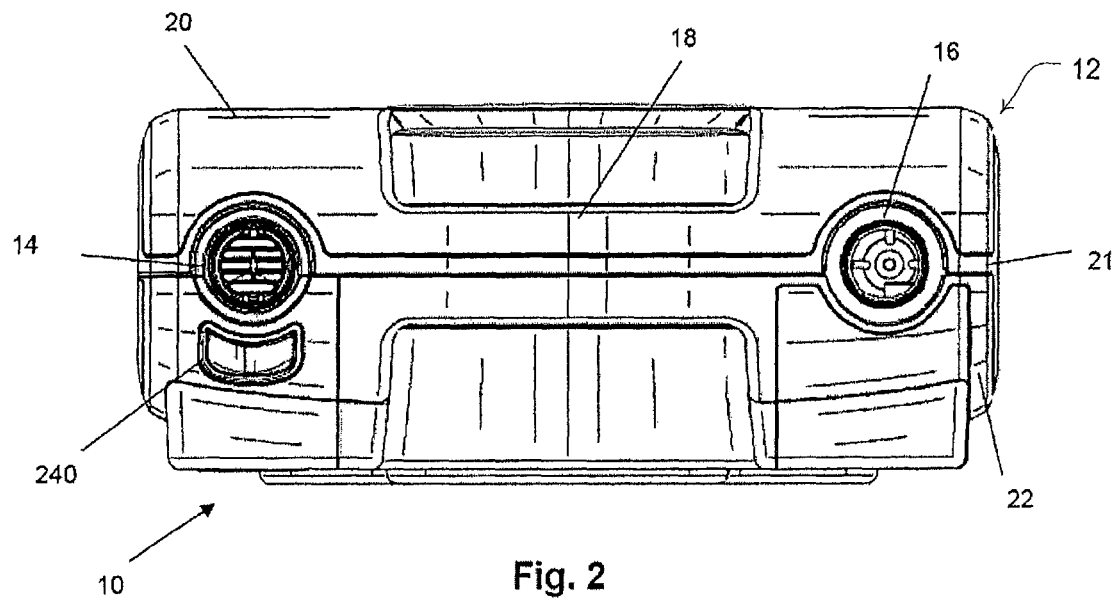
FIG. 2 is a view of the front of the ventilator apparatus of FIG. 1.

FIG. 2 illustrates a ventilator 10 including an expiratory gas routing module adapted for removable insertion within the expiratory portion of the apparatus. In such a case, the expiratory portion may be a compartment of the apparatus as will be explained in more detail herein with reference to the figures. The compartment includes a plurality of gas port connections in a particular fixed interface configuration (e.g., a molded structure) to permit insertion of different gas routing modules within the compartment using mating gas ports interfaces. As explained in more detail herein each expiratory gas routing module may be configured with several distinct internal structural flow channels or gas pathways that may serve different functions, and may do so without tubes, depending on the purpose of the module. The pathways of the module lead to a fixed gas ports interface of the module for coupling with the structure of the gas ports interface of the expiratory portion compartment such as with a seal. As such, the module may be easily inserted into the expiratory portion to couple with the expiratory portion's gas ports interface so that the respiratory pressure apparatus can deliver different treatment protocols in conjunction with the inserted module. In this sense, the gas ports interface of the module has a standardized configuration (size and positional location) to permit a simple insertion of each different module into the complementary gas ports interface of the expiratory portion compartment depending on the desired functionality of the respiratory treatment apparatus. The module structure and the compartment structure with their fixed complementary gas ports interfaces permit the module to be plugged or installed into the compartment such that multiple gas connections may be fitted together substantially simultaneously rather than separately plugging in tubes for each gas port. Such complementary fixed structural interfaces for multiple gas ports helps to simplify assembly. Assembly may also be accomplished more rapidly since the structure of the module will only fit in one aligned position within the structure of the compartment. Inaccurate gas couplings, such as when tubes may be connected to the wrong ports, may thus be avoided.

Figure 22B:
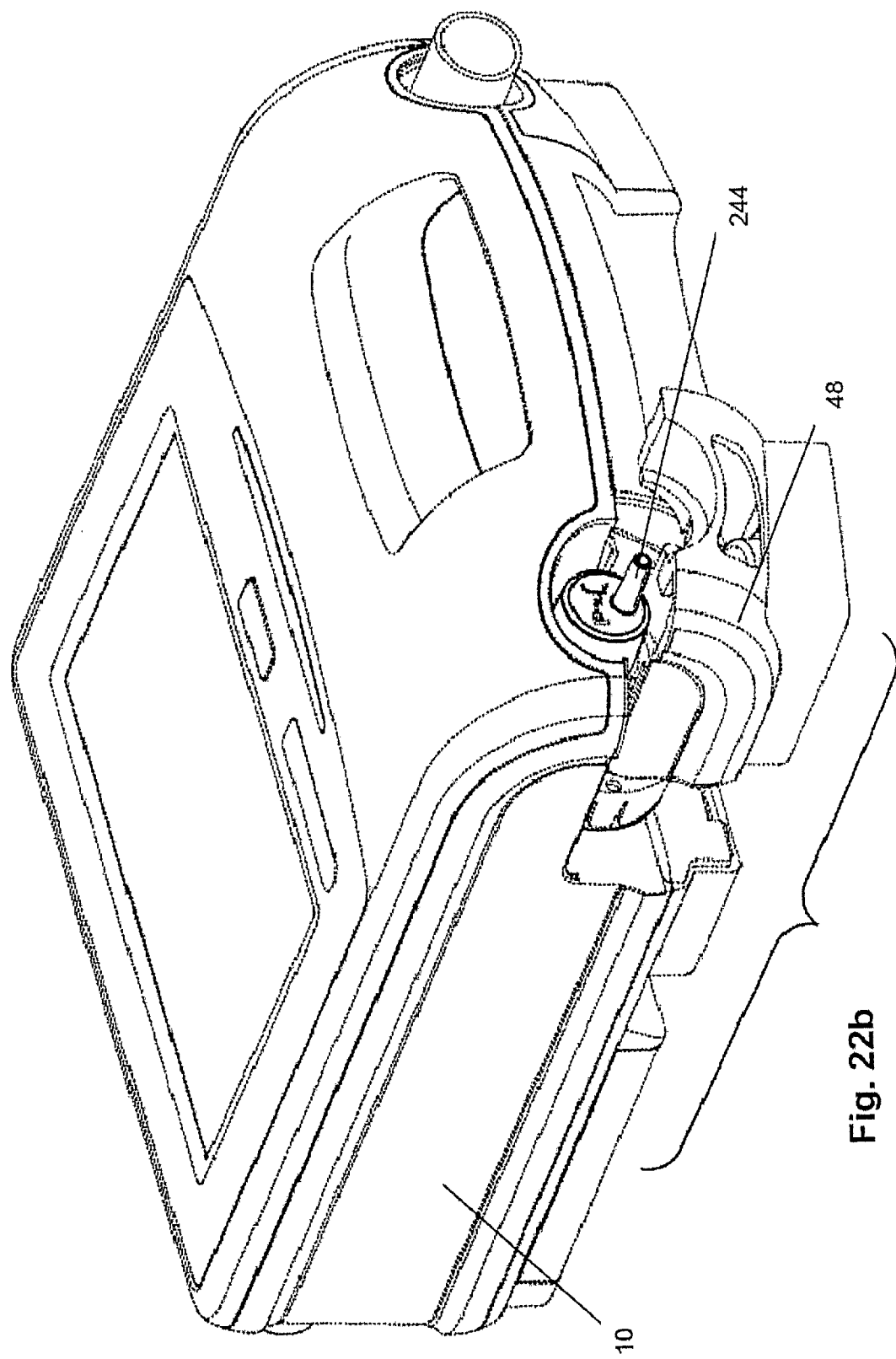
Figure 22C:
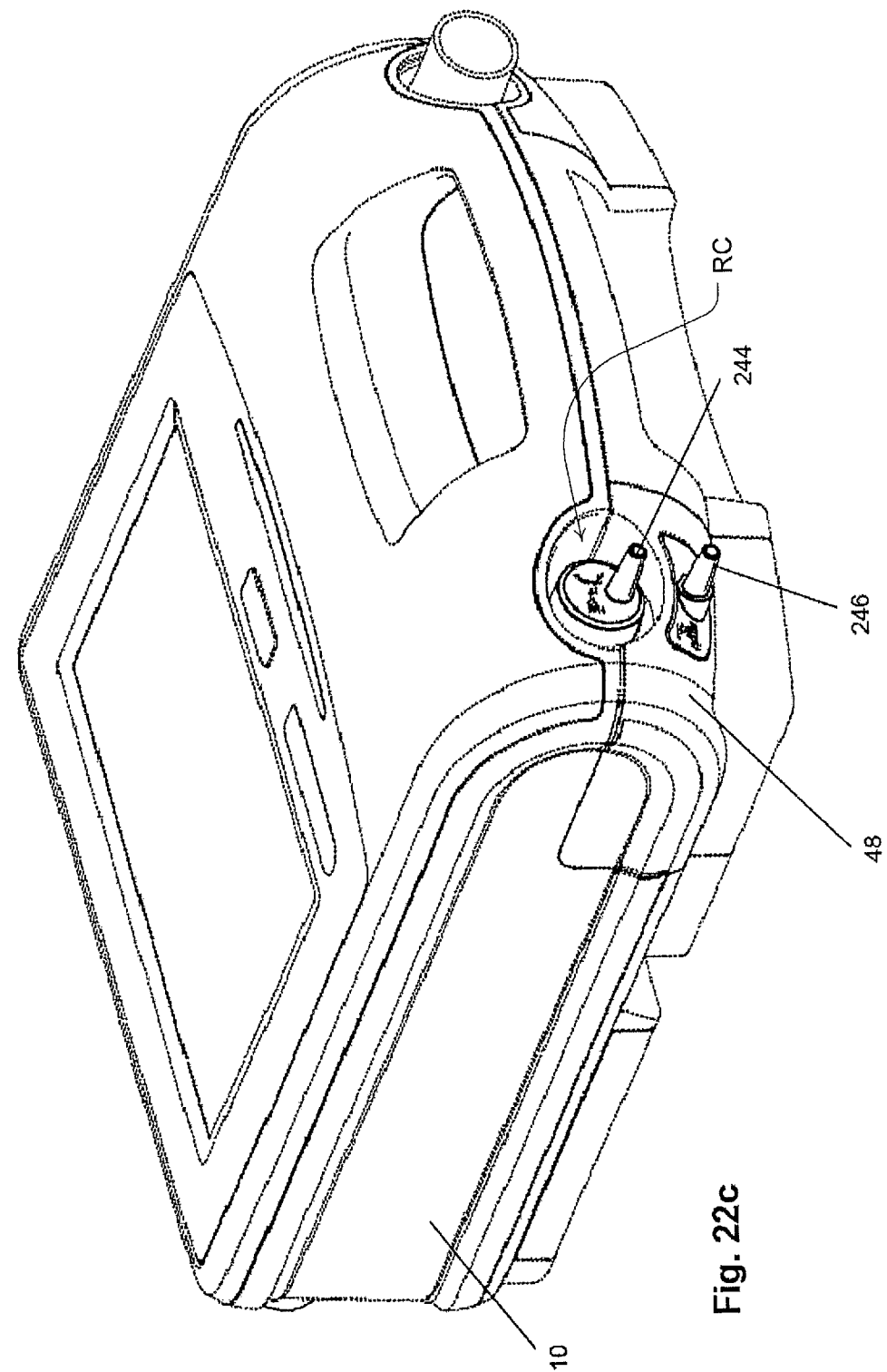
Figure 23:
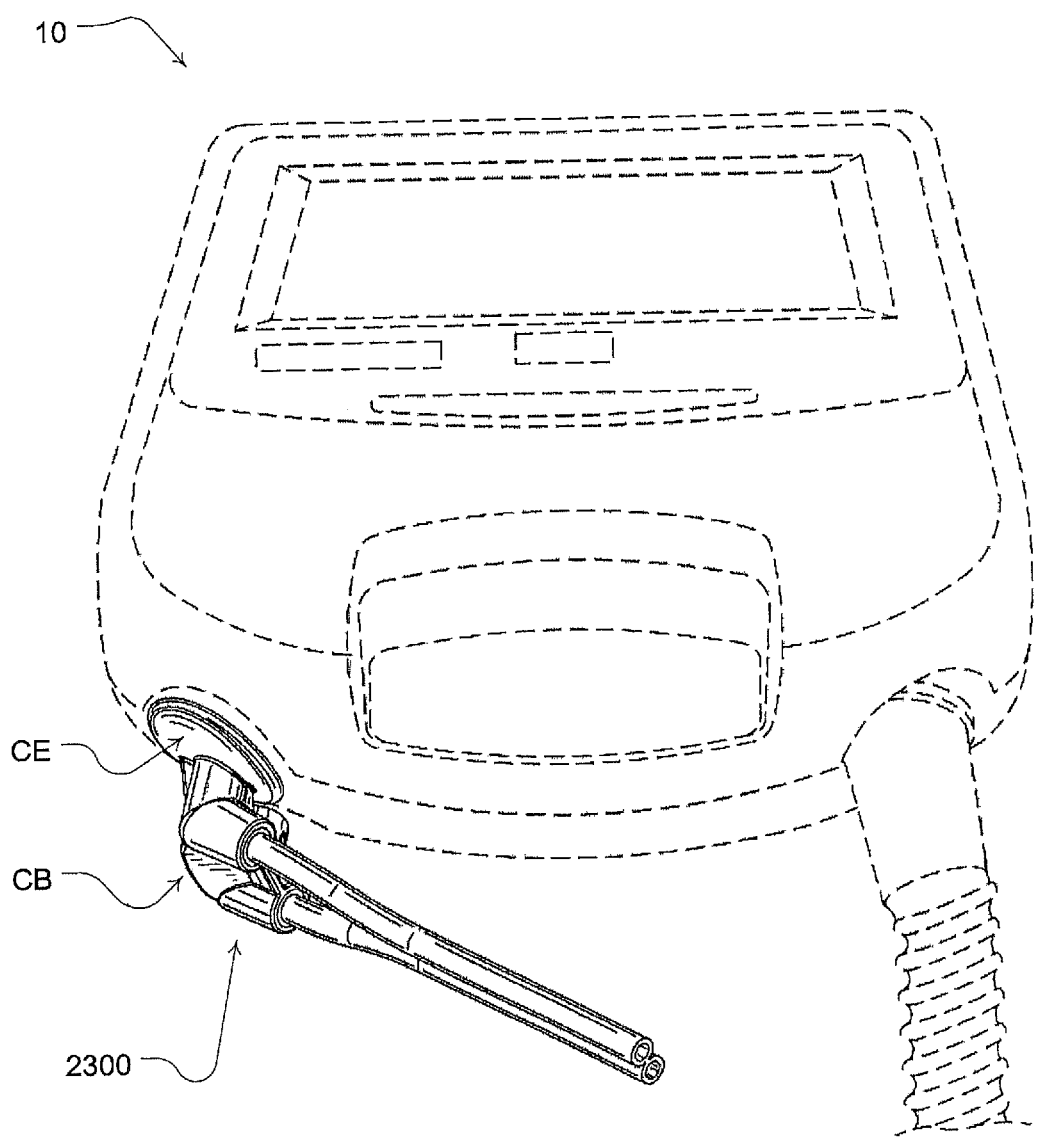
FIG. 23 shows a conduit coupler adapted for connection with an expiratory adapter in a ventilator of the technology.
Figure 24:
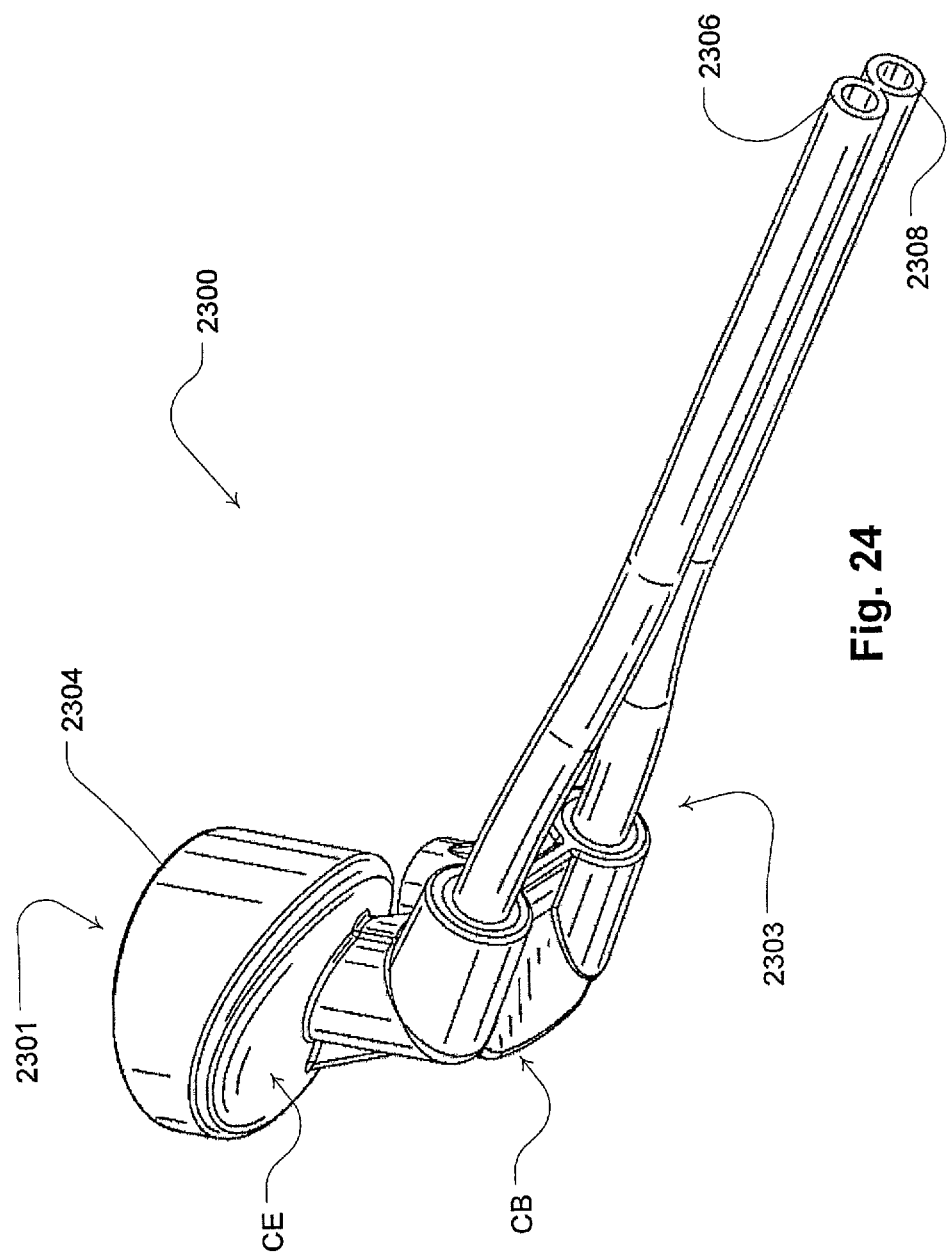
FIG. 24 shows the coupler of FIG. 23 de-coupled from the ventilator.
Figure 28:
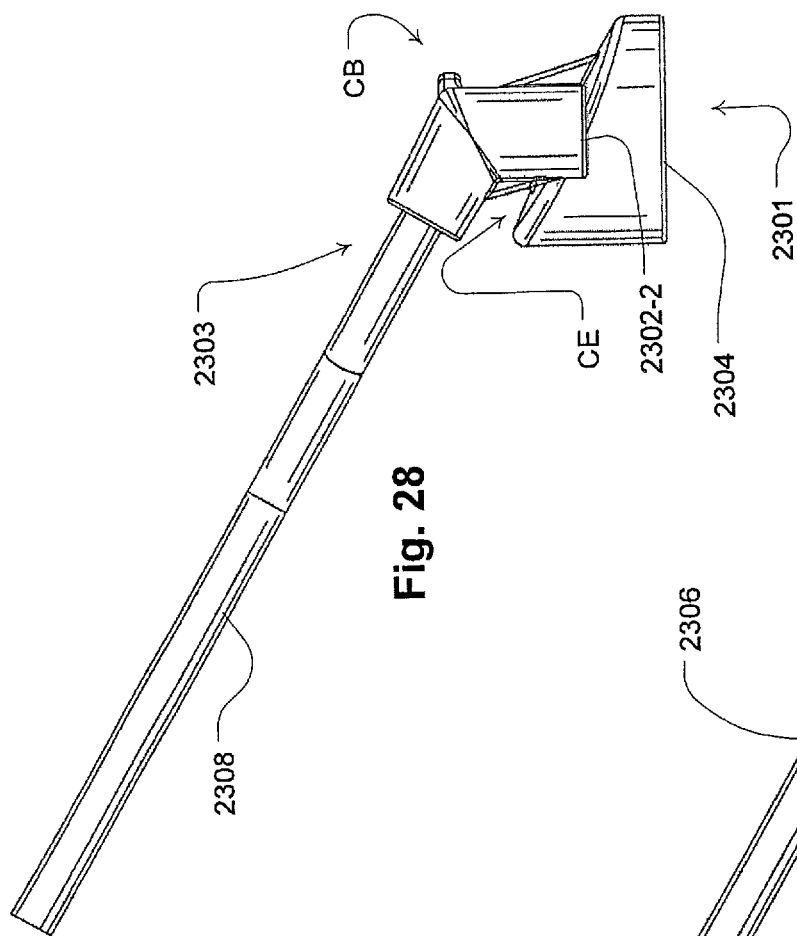
FIGS. 27 and 28 are left and right views respectively of the coupler of FIG. 23.
Figure 27:
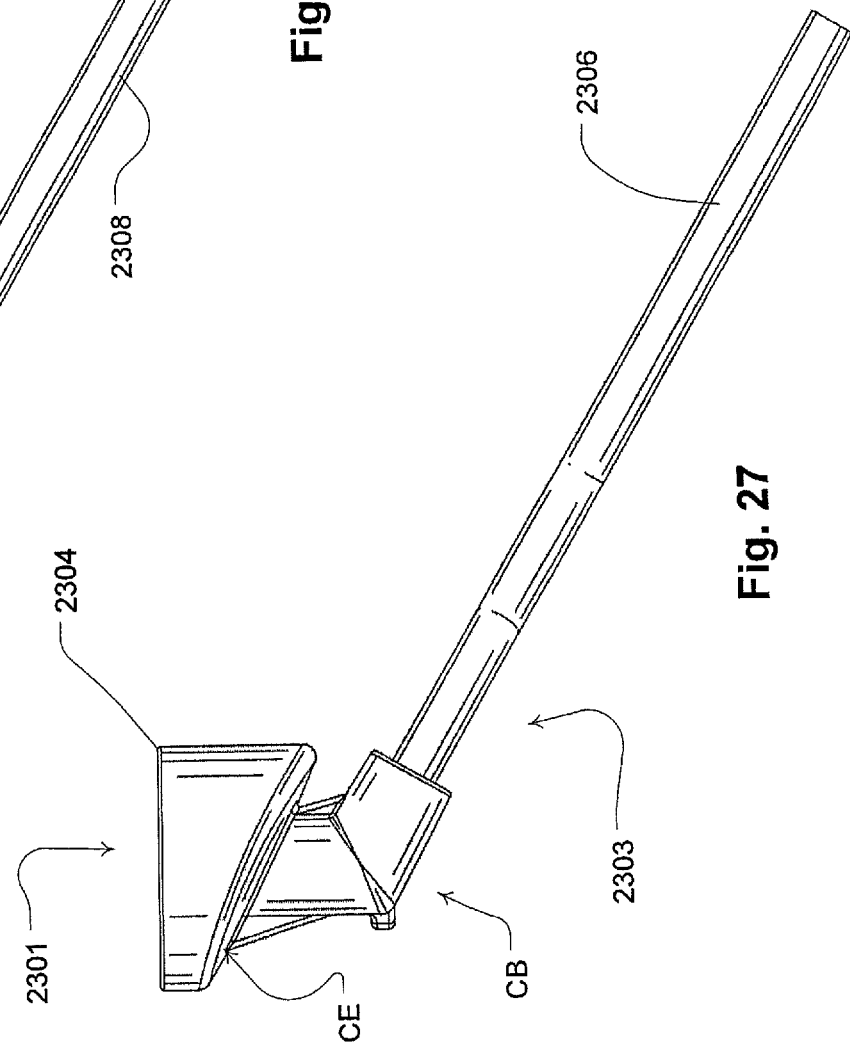

In the illustration of FIG. 2, the expiratory gas routing module is an expiratory valve 200 connectable within the expiratory portion 31. The expiratory valve, which is described in more detail herein in reference to FIGS. 19 and 20, includes an expired gas output port 240. Optionally, the expiratory gas routing module may be an expiratory adapter 202 (not shown in FIG. 2 but which is described in more detail herein with reference to FIGS. 21 and 22), which also fits within the expiratory portion 31. The expiratory adapter 202 includes a Positive End Expiratory Pressure (PEEP) control port 246 that may be located on the front of the housing 12 and proximate to the adapter pressure inlet port 244. The PEEP control port may be used in conjunction with the adapter pressure inlet port 244 when the ventilator is used in a PEEP operating mode.

Figure 3:
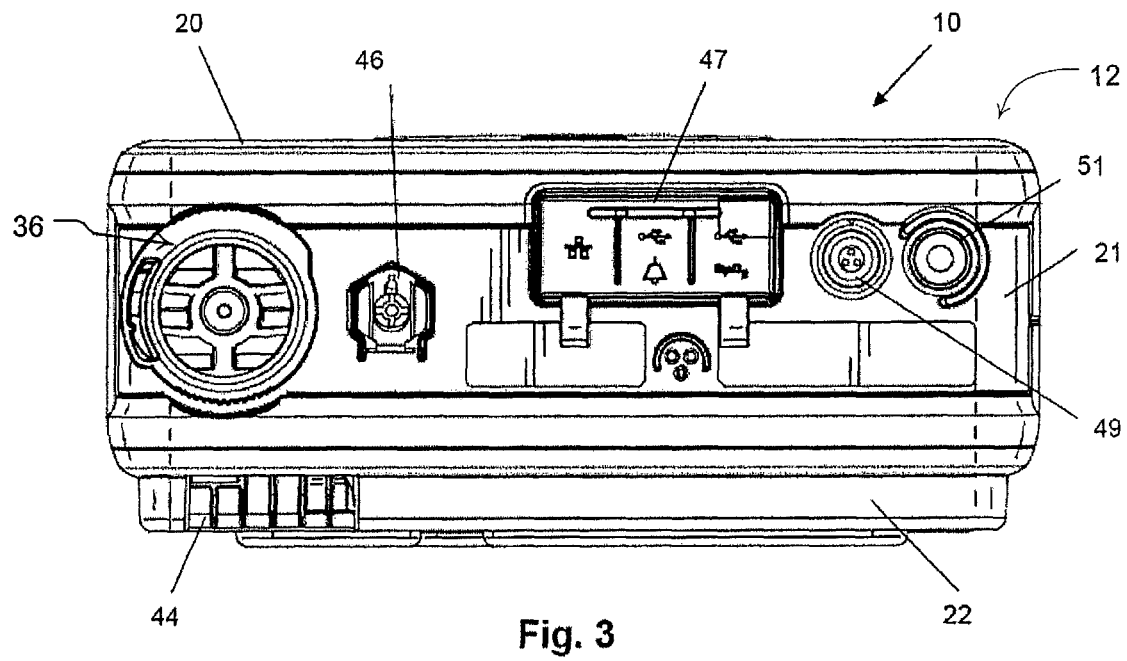
FIG. 3 is a rear view of the ventilator apparatus of FIG. 1.

As shown in FIG. 3, the rear of the housing 12 may include an a filter assembly 36 (described in more detail herein in reference to FIGS. 9, 10 and 11). Air to be pumped into the lungs of the patient is drawn into the air inlet associated with the filter assembly. The air passes through a permeable filter membrane in the filter and enters an air passage for air flowing to the patient.

The rear of the housing may include data connections 47 for communications with digital devices such as computer networks, alarm systems, a pulse oximeter (e.g., spO$_2$) and digital recording media. An electrical power connection 49 and an on-off switch 51 may also be positioned at the rear of the housing. A input grill 44-I provides an inlet for air to cool components and permit dissipation of the heat generated by operation of the internal components (e.g., blower motors and CPU). Movement of the heated air across internal components may be driven by a cooling fan 68 in the housing, which may be near a heated air output grill 44-O (shown on bottom of housing in FIG. 4). In addition, an oxygen (O$_2$) inlet port 46 may be at the rear of the housing, which permits coupling with an oxygen source.

Figure 4:
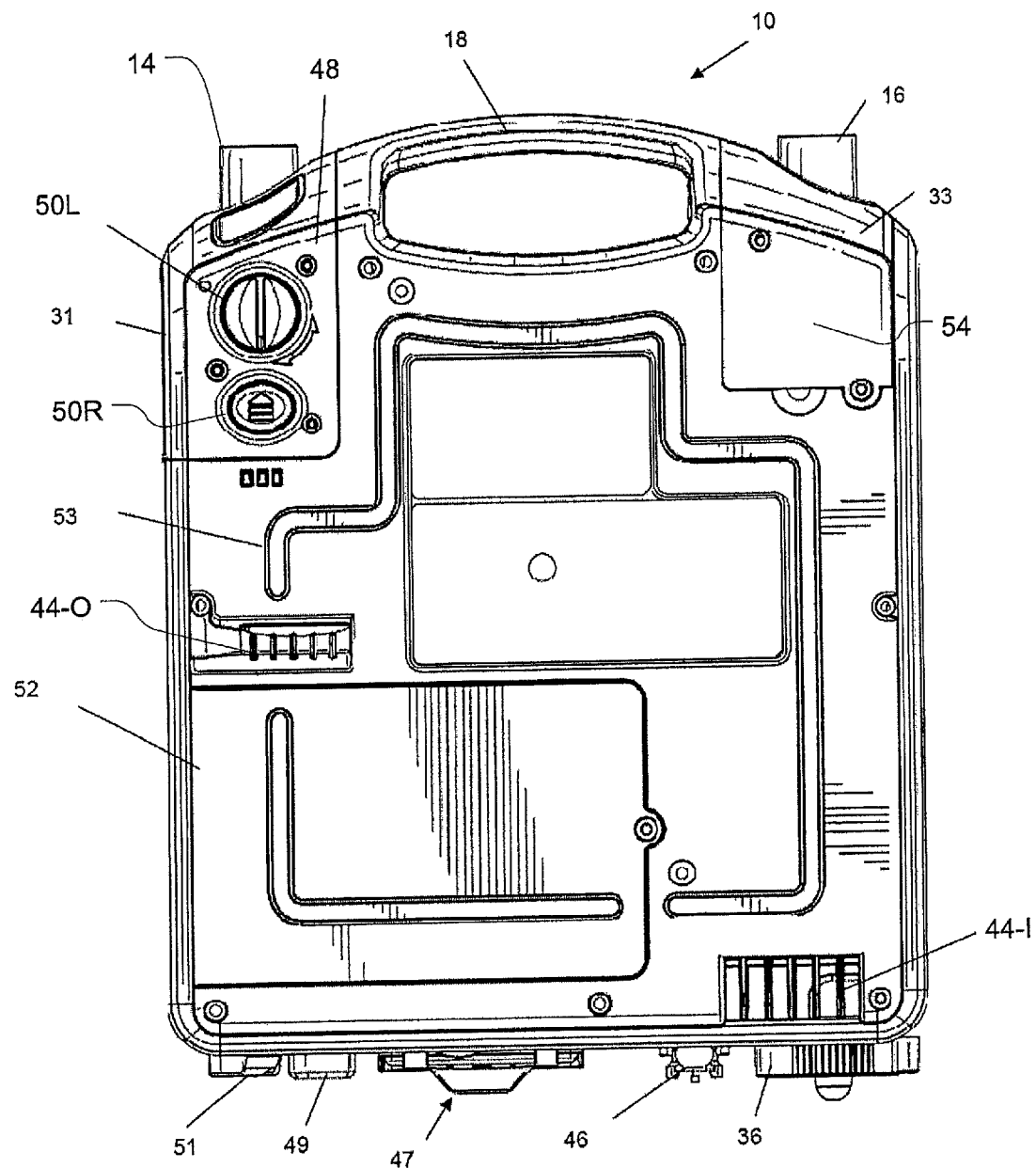
FIG. 4 is a bottom view of the ventilator apparatus of FIG. 1.

FIG. 4 shows a bottom of the ventilator housing. The removable expiratory cover 48, which serves as an external access hatch, provides access to and protection for the compartment of the expiratory portion or section of the housing. Removing the expiratory cover 48 provides access to any inserted expiratory gas routing module as well as the expiration air inlet port 14. It also allows for easy removal and replacement of the expiratory gas routing module such as the expiratory valve or expiratory adapter. The expiratory cover 48 may be tightened to the housing to reduce excess play by a latch dial 50L that may be turned with the fingers. Optionally, in some embodiments, the latch dial might serve to lock the latch from releasing. An optional latch release button 50R may be operated to disengage the expiratory cover. The release button 50R may be depressed to unlatch the expiratory cover 48. A skilled addressee would understand that alternative ways of removably securing and coupling the expiratory cover 48 to the housing may also be utilized. The bottom of the ventilator housing may also have removable battery cover 52 for a replaceable battery and an oxygen sensor cover 54 which may be removed to access an oxygen sensor 64.

Figure 8:
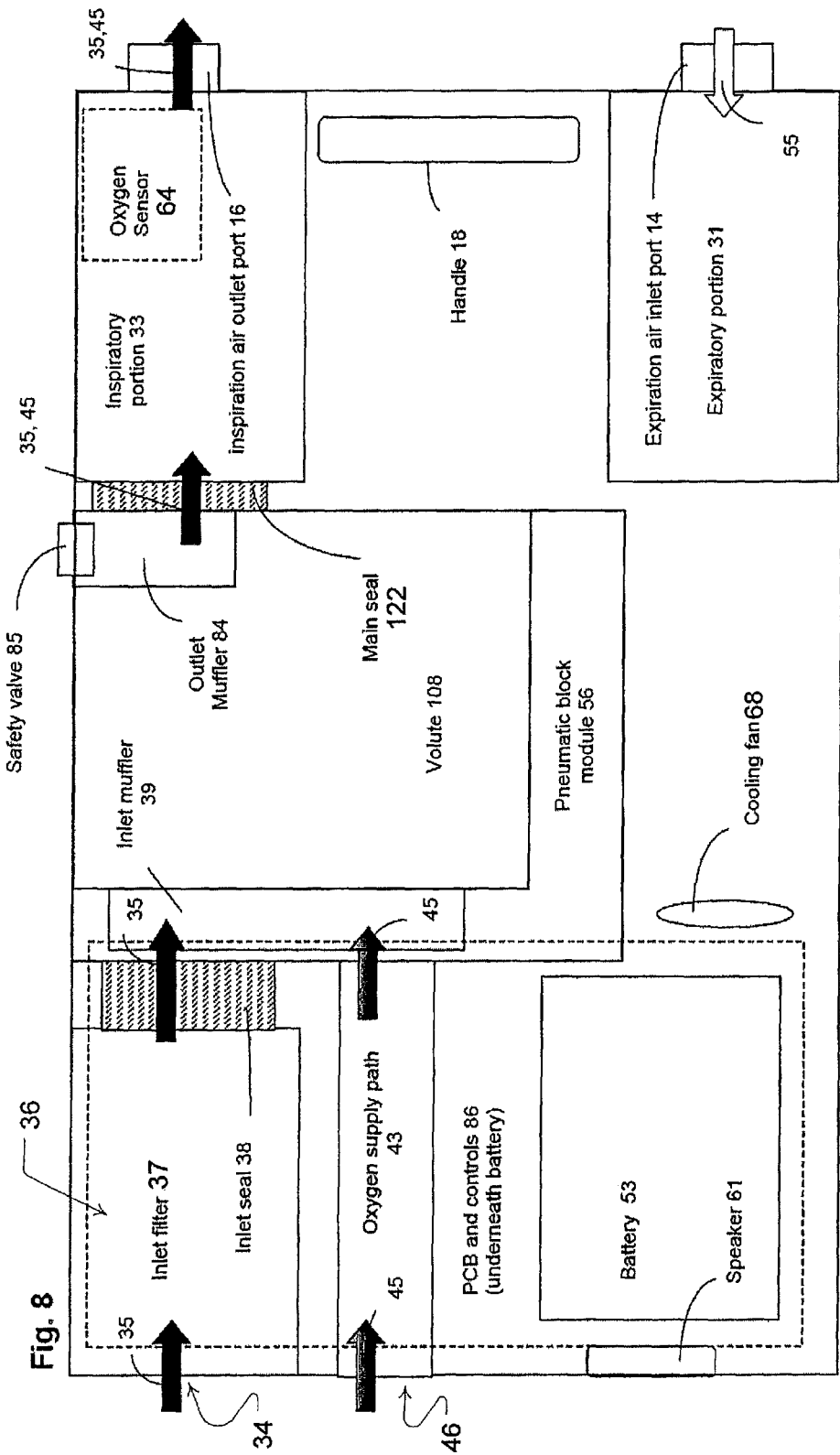
FIG. 8 is a schematic of the interior of the housing of a ventilator apparatus according to an example of the disclosed technology.

FIG. 5a shows a construction of the chassis 21 which may be organized according to the schematic diagram of the interior of the housing 12 shown in FIG. 8, which indicate the location of many of the components of the ventilator when installed in the casing. As is evident from at least FIGS. 8 and 5a, the interior of the housing is arranged with one or more dividers or walls to create various compartments that provide discrete sections for components that may serve as functionally compartmentalized areas, such as the inspiratory portion or the expiratory portion, the oxygen sensor compartment etc. Such a specialization of components into discrete areas can serve to simplify assembly and servicing of the apparatus as well as provide a way to segregate components to impede access to some components when access is only necessary for other components.

For example, the tubes and air passages of a pneumatic block module 56 (not shown in FIG. 5a) that includes one or more blowers for generating treatment pressure may be easily removed and replaced from the pneumatic block mounting seat 58 (shown in FIG. 5a) in the housing. The pneumatic block module 56 may be inserted into such a molded seat in the chassis 21 assembly and may rest on shock absorbers or elastomeric supports to protect the module and/or reduce sound vibration. The walls of the seat, which conform to the shape of the perimeter of the pneumatic block, may serve to align and support the block in its particular assembled position. As shown in FIG. 8, the pneumatic block module is seated such that its air passages are aligned with the filter assembly 36 at the air inlet 34, the inspiration outlet port 16 and the oxygen supply path 43. Arrows indicate the air flow 35 path and arrows indicate the oxygen flow 45 path through the ventilator 10. The air flow 35 enters via the air inlet 34 and travels through the filter assembly 36 and inlet seal 38 into an inlet muffler 39 of the pneumatic block module 56. Optionally an oxygen source may be attached at the oxygen inlet port 46 and the oxygen flow 45 is directed through the oxygen supply path 43 and an oxygen seal into the pneumatic block module 56 where it is combined with the inlet air flow 35 within the inlet muffler 39. Within the pneumatic block module 56 the air flow 35 is pressurized by a main blower 104 as described in more detail below. The pressurized air/oxygen flow 35, 45 are directed out of the pneumatic block module 56 via outlet muffler 84 and through the main seal 122 into the inspiratory portion 33 and then out the inspiration outlet port 16 to be delivered to the patient interface (not shown) via an air delivery conduit (not shown).

An oxygen sensor 64, which may be located in an oxygen sensor compartment of the inspiratory portion 33, measures the amount of oxygen being delivered to patient. The oxygen sensor 64 may be mounted in the housing 12 such that it is easily replaced and adjacent the inspiration outlet port 16. The oxygen sensor detects the oxygen level of the air being pumped to the patient. Data from the oxygen sensor may be used to trigger alarms related to oxygen concentration and to provide data to the microprocessor to display the oxygen concentration on the user interface. The amount of oxygen supplied may be controlled by adjusting the known volumes of air and oxygen supplied to the patient. However, the oxygen sensor may also optionally be used to regulate the amount of supplemental oxygen to be supplied through the oxygen inlet port 46.

An oxygen sensor cover 54 (shown in FIG. 4) on the bottom of the housing is removable to provide access to the oxygen sensor contained within an oxygen sensor compartment of the housing. The oxygen sensor fits in a mount within the housing and adjacent to the inspiration outlet port 16. A portion of the air flowing through the inspiration outlet port 16 is sensed by the oxygen sensor. The sensor generates data signals indicating the oxygen level of the gas. The data is conveyed by wire to a data connection which conveys the data to a processor. The processor analyzes the data to determine the amount of supplemental oxygen to be added to the air being pumped to the patient.

The oxygen source may be a low pressure oxygen supply or a high pressure oxygen supply. For the supply of a high pressure oxygen source an oxygen regulator (not shown) may be located within the oxygen supply path 43 to reduce the pressure from the high pressure oxygen source before the oxygen enters the inlet muffler 39. The oxygen inlet port 46 may be adapted to couple to a range of different oxygen connection adaptors to allow the connection of different types of oxygen connectors used in different jurisdictions including but not limited to male or female diameter index safety system (DISS), sleeve indexing system (SIS), National Institute of Standards Technology (NIST) and Association Francaise De Normalisation (AFNOR).

In an alternative arrangement (not shown) a high pressure oxygen source may be provided after the main blower 104 such as within the outlet muffler 84 where it is mixed with the pressurized air source. In some examples the high pressure oxygen may be used to provide the pressure source for the gas flow to the patient.

Although the pneumatic block module 56 is schematically shown as a rectangular shape it is to be understood that the pneumatic block module 56 may have any shape including a non-symmetrical shape that conforms to a seat in the housing and would minimize the possibility that the pneumatic block module 56 is improperly inserted into the housing.

The main printed circuit board (PCB) or PCB 86 (shown in FIG. 8), may be assembled and mounted to the chassis 21 and located between the chassis 21 and the lower housing case 22. The electronic components of the main board may include a processor, electrical connectors to convey data signals from the pneumatic block module 56 such as an electrical power and data connector for the blower which provides pressurized air to the inspiration outlet port 16. In this regard, the electrical connectors provide power and signal paths between the electronic components on a PCB in the pneumatic block module 56 and the electronic components on the main PCB in the housing. The electronic components of the main board may also include a data and power connector for any sensors, such as the oxygen sensor. The electronic components in the housing may control a generation of images for the display device, sound signals for a speaker 61, such as for producing audible alarms, detect signals from pressure and oxygen sensors, and control the rotational speed of the blower.

As previously mentioned, the chassis 21 may include a pneumatic block mounting seat 58 that may conform to the perimeter of the pneumatic block module 56. The chassis 21 may also provide a filter seat and/or a compartment (shown as inlet filter support 176) for the inlet filter assembly 36, and other mounting seats for the low pressure oxygen connection assembly, a cooling fan 68, and a deformable expiratory seal 70, which is described in more detail herein with reference to FIG. 18. The chassis 21 may also include embedded or integrated air passages and ports that may be molded within the chassis structure such as for conveying air between sections or compartments of the chassis. For example, air at a known pressure may be channeled through passages of the chassis from the pneumatic block module to the PEEP air supply.

Filter Assembly 36

Figure 9A:
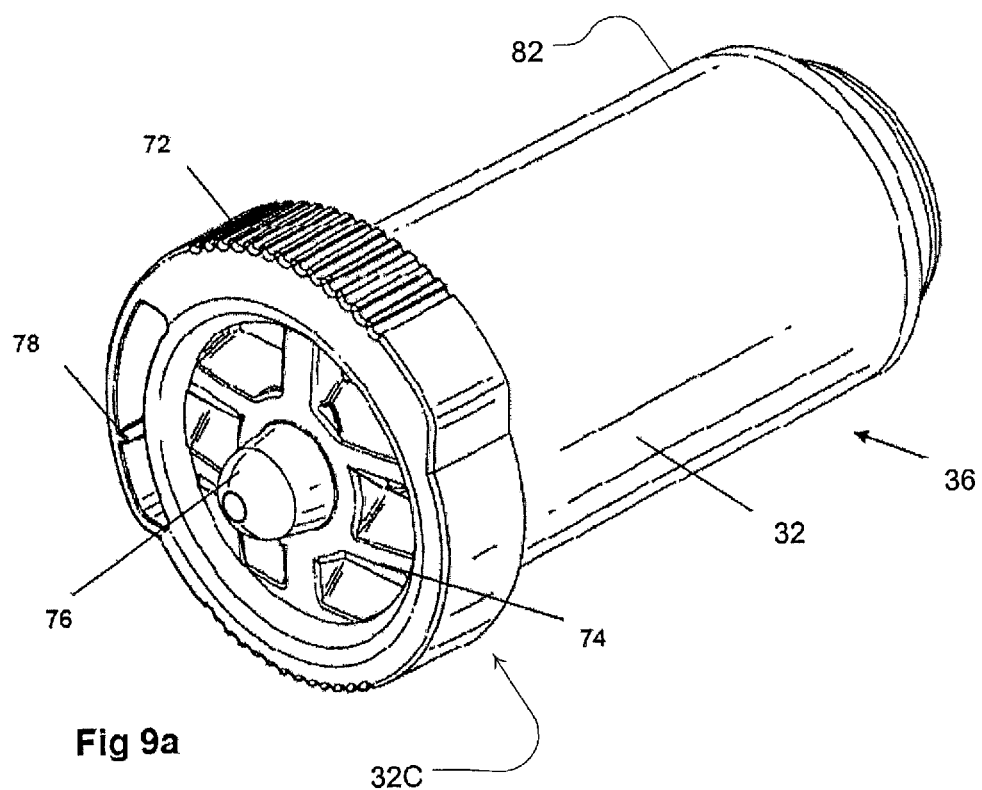
FIGS. 9a to 9c are perspective, front and rear views respectively of a filter assembly according to an example of the disclosed technology.
Figure 9B:
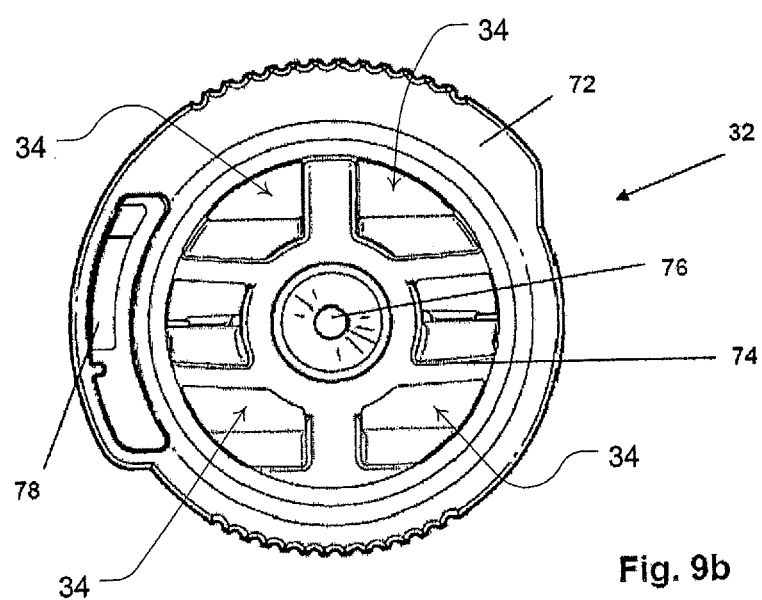
Figure 9C:
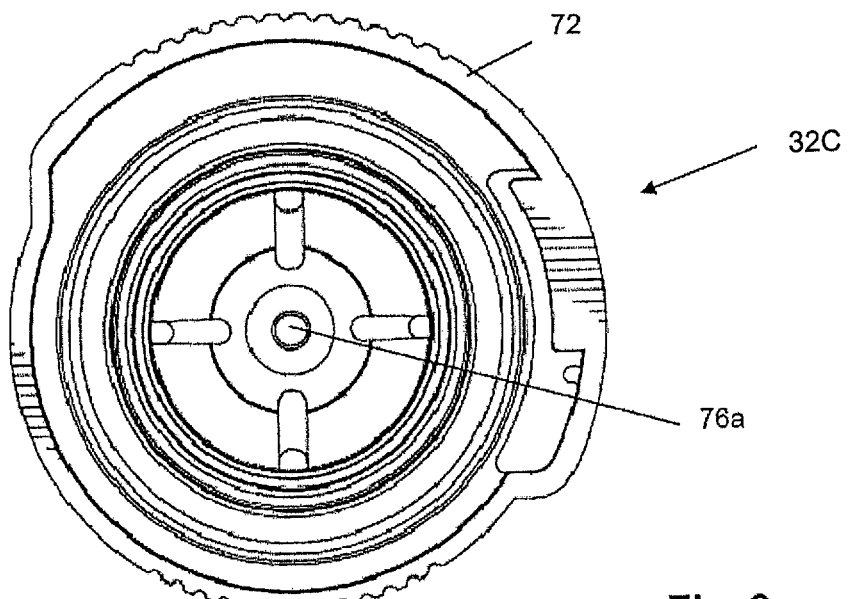
Figure 10A:
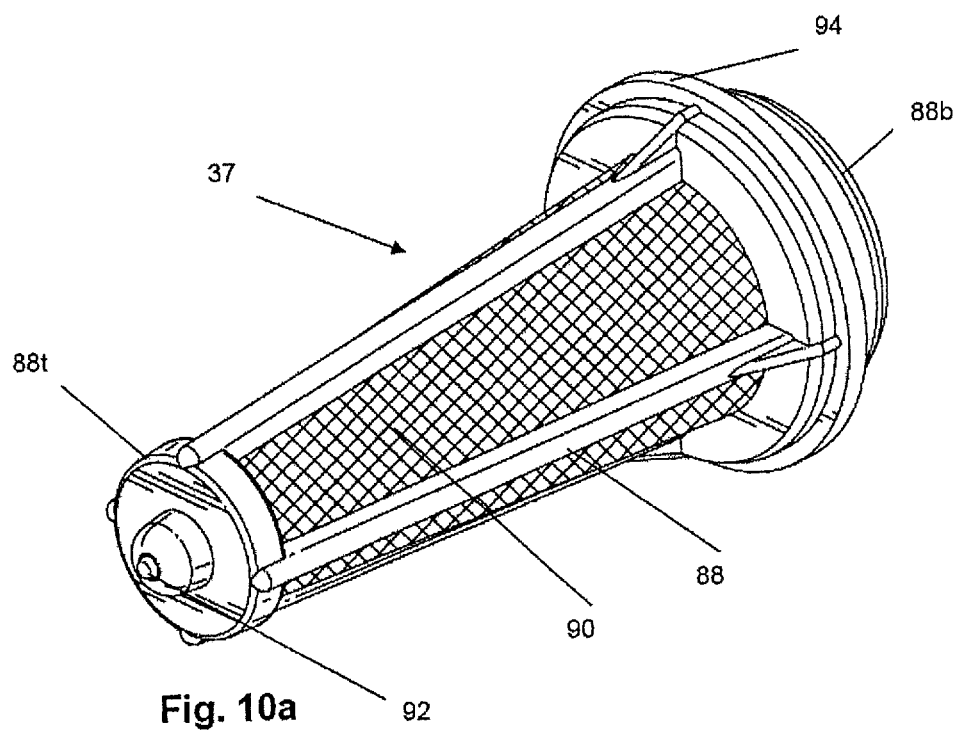
FIGS. 10a to 10d are front perspective, back, front and back perspective views respectively of an inlet filter according to an example of the disclosed technology.
Figure 10B:
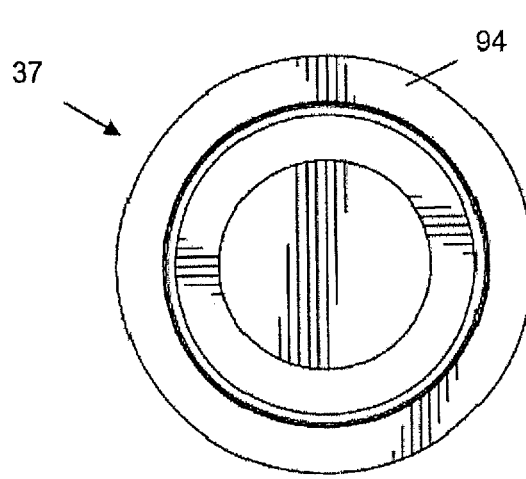
Figure 10C:
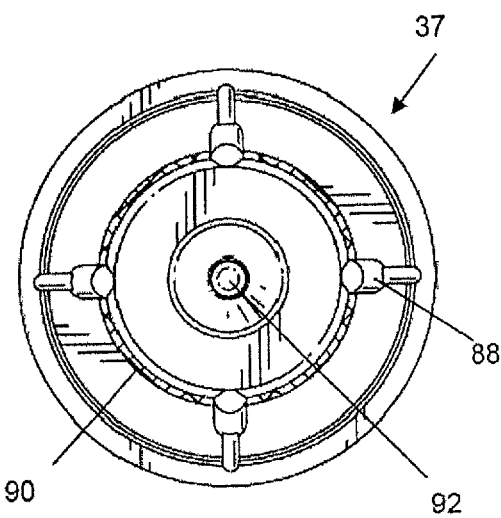
Figure 10D:
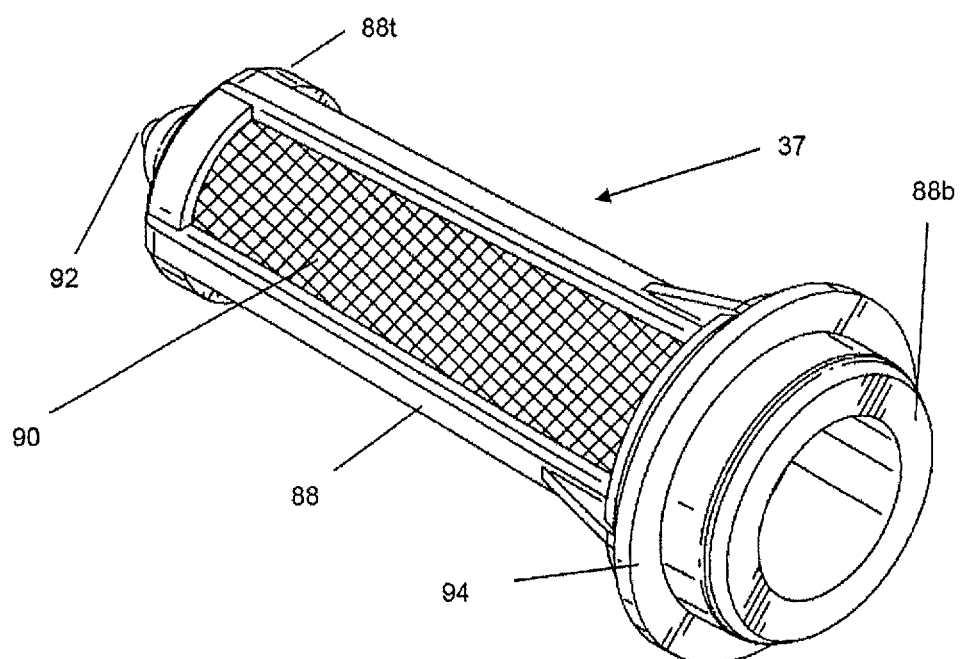

FIG. 9a shows a perspective view of a filter assembly 36 and FIGS. 9b and 9c show front and rear views of the filter assembly 36 respectively. The filter assembly 36 includes an inlet filter housing 32 adapted to receive an inlet filter 37 (see FIG. 10a) therein. As seen in FIG. 9b the air inlet 34 for the ventilator 10 is formed in the front outer surface of the inlet filter housing 32. The air inlet 34 comprises a grill or grate 74 configured to prevent large particles from entering the filter assembly 36. Preferably the grate 74 is angled downwards to substantially prevent or reduce water ingress into the ventilator. The downwardly angled grate is structured to direct any water to run off and not enter the inlet filter assembly 36. The grate 74 also prevents objects or fingers from being inserted into the filter assembly 36.

A housing protrusion 76 extends from the outer surface of the air inlet 34 and is structured to prevent objects from completely blocking the air inlet 34. The opposing surface of the housing protrusion 76 forms a cone 76a (shown in FIG. 9c) within the filter housing cover 32C that is adapted to receive a corresponding filter protrusion 92. A collar 72 surrounds the air inlet 34 and provides a locking mechanism such as a bayonet, threaded or screw locking mechanism to secure the filter assembly 36 to the ventilator housing 12 as described in more detail below.

The inlet filter housing 32 may be formed as a cylinder portion 82 that is configured to receive the inlet filter 37. The cylinder portion 82 preferably has a substantially constant diameter of about 20-60 mm, more preferably about 30-40 mm, such as about 34 mm, 35 mm or 36 mm along the length of the cylinder portion 82. The length of the cylinder portion may provide a muffling function to reduce noise being transmitted back through the inlet. The length of the cylinder portion is preferably about 30-100 mm, more preferably 50-80 mm, or 60-70 mm, such as 60 mm, 61 mm, 62 mm or 64 mm. However, it is to be understood that a cylinder portion 82 may be formed with other dimensions.

FIGS. 10a to 10d illustrate the inlet filter 37 according to an example embodiment. The inlet filter 37 comprises a filter cage 88 having a porous filter material 90 coupled thereto. The filter cage 88 provides a structural support for the filter material 90 and includes a tip end 88t and a base end 88b. The inlet filter 37 may have a frustoconical shape to maximize the filtering area while providing a relatively small opening on the exterior of the ventilator housing for the incoming air. The filter material 90 may be fixed to the filter cage 88 by injection over moulding the cage onto the filter material. However, other methods of coupling or fixing the filter material 90 to the filter cage 88 may be implemented.

Optionally, the porous filter material 90 may be arranged in pleats or be unpleated and it may form the sidewalls of the frustoconical shaped inlet filter 37. The filter material 90 filters atmospheric air flowing in through the air inlet 34 to remove dust and other particles from the air before the air is pumped through the ventilator 10 and subsequently to a patient. The filter material may optionally have a filtration cutoff level of at least 10 micrometer (µm) filters, such as 8 µm, 7 µm or 6 µm. The portion of the inlet filter 37 including the filter material 90 preferably has an diameter of about 10-30 millimeters (mm), more preferably 15-20 mm, such as 17-19 mm or 18 mm at the tip end 88t of inlet filter and a diameter of about 20-55 mm, more preferably about 25-35 mm, such as about 30 mm, 31 mm or 32 mm at the wider base end 88b of the inlet filter.

To assemble the filter assembly 36, the inlet filter 37 is inserted into the open or inner end of the cylinder portion 82 of the inlet filter housing 32 and may have an interference fit. A filter flange 94 at the base end 88b of the inlet filter 37 forms a stop against the outer rim of the open or inner end of cylinder portion 82 to provide for the correct level of insertion. To correctly align the inlet filter 37 within the inlet filter housing 32 a filter protrusion 92 at the tip end 88t of the inlet filter 37 is received within the cone 76a within the filter housing cover 32C.

The filter cage 88 and the inlet filter housing 32 may be formed of a plastic material such as polycarbonate or polypropylene, and may be formed by moulding. The filter material 90 may be a hypo-allergenic air filter material, such as a polyester fibre that has been needled and thermally bonded. Optionally, the filter material may be, for example, a foam, paper, polyester, woven, unwoven, pleated, unpleated etc.

Figure 11B:
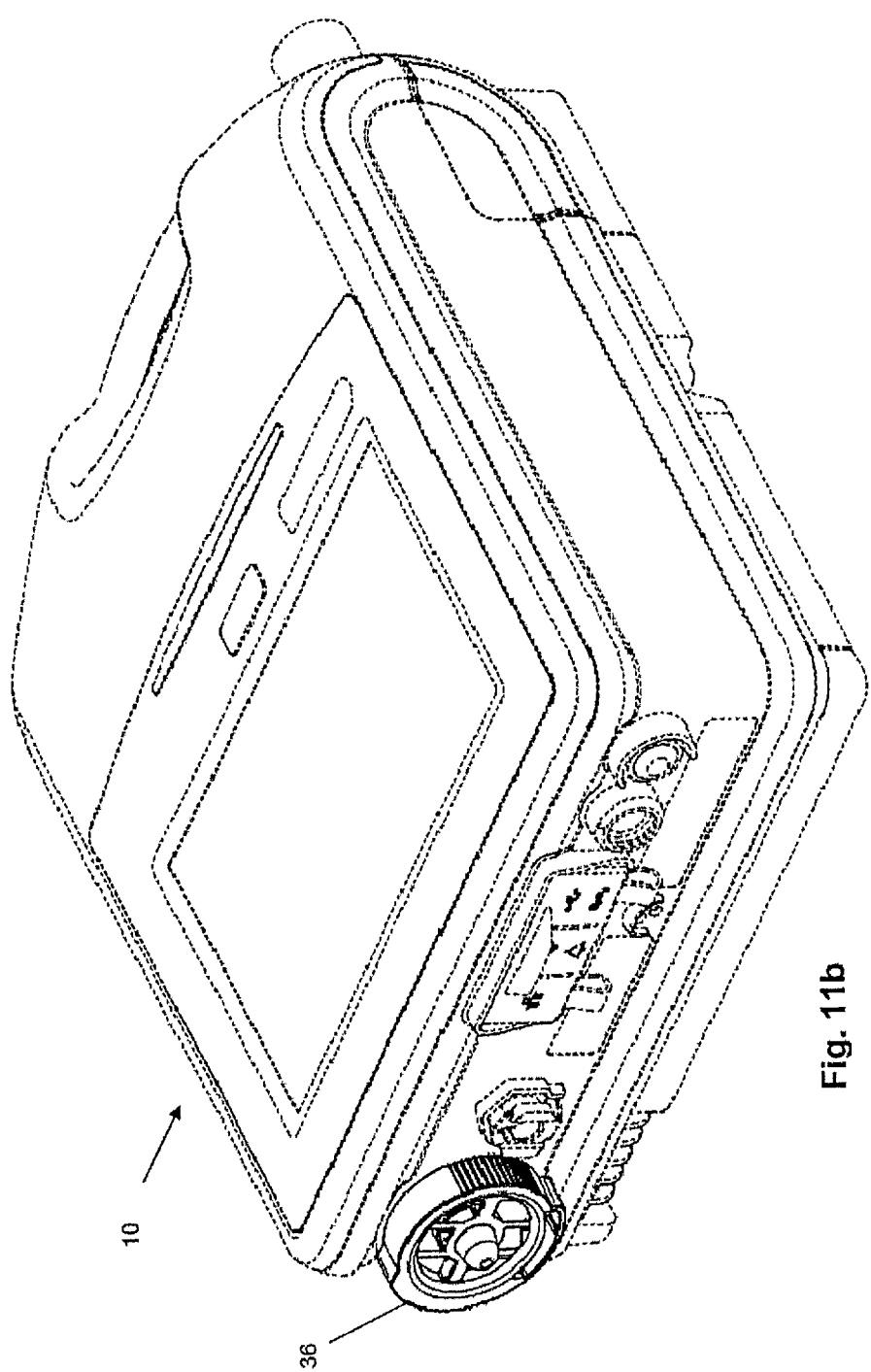

As illustrated in FIGS. 11a and 11b, the filter assembly 36 is structured to be removably inserted into an inspiratory portion compartment of the chassis 21 of the housing 12 of the ventilator 10 to allow easy replacement and inspection of the inlet filter 37. Thus, it may be inserted and removed from a filter compartment FC of the chassis. The collar 72 of the inlet filter housing 32 may include one or more lug or pin 78 to engage an inlet opening 80 in the rear of the housing 12. The inlet opening 80 on the rear of the ventilator comprises one or more corresponding divot or slot 80a into which one or more pins or lugs of the cover may engage. Other removable fastening mechanisms such as a threaded fastener, screw, snap locks etc, may be used to removably couple the filter assembly 36 to the ventilator housing 12.

To insert and secure the filter assembly 36 within the ventilator housing 12 the filter assembly 36 is inserted into the inlet opening 80 in the ventilator housing 12 and the collar 72 is turned, preferably by hand, to engage the lug/pin 78 of the filter assembly 36 to the divot or slot 80a of the ventilator housing 12 to securely lock the filter assembly 36 to the ventilator housing 12 as shown in FIGS. 11a and 11b. The filter assembly 36 sealingly engages with the inlet seal 38 within the ventilator 10 to form an airtight radial seal. The inlet filter 37 includes a lead-in taper on the base end 88b that facilitates the engagement with the inlet seal 38. The inlet seal 38 ensures that the incoming air flow 35 is limited to the air path within the ventilator and cannot contaminate the remainder of the chassis.

To remove the filter assembly 36 the collar 72 is turned in the opposite direction to disengage the lugs or pins 78 from the slot 80a to allow the filter assembly 36 to be pulled out of the filter compartment of the ventilator housing 12. Thus, the complete filter assembly 36 may be completely replaced to replace the inlet air path, for example for multiple patient use. Alternatively only the inlet filter 37 may be replaced as required for cleaning or maintenance of the ventilator.

Pneumatic Block Module—56

Figure 13:
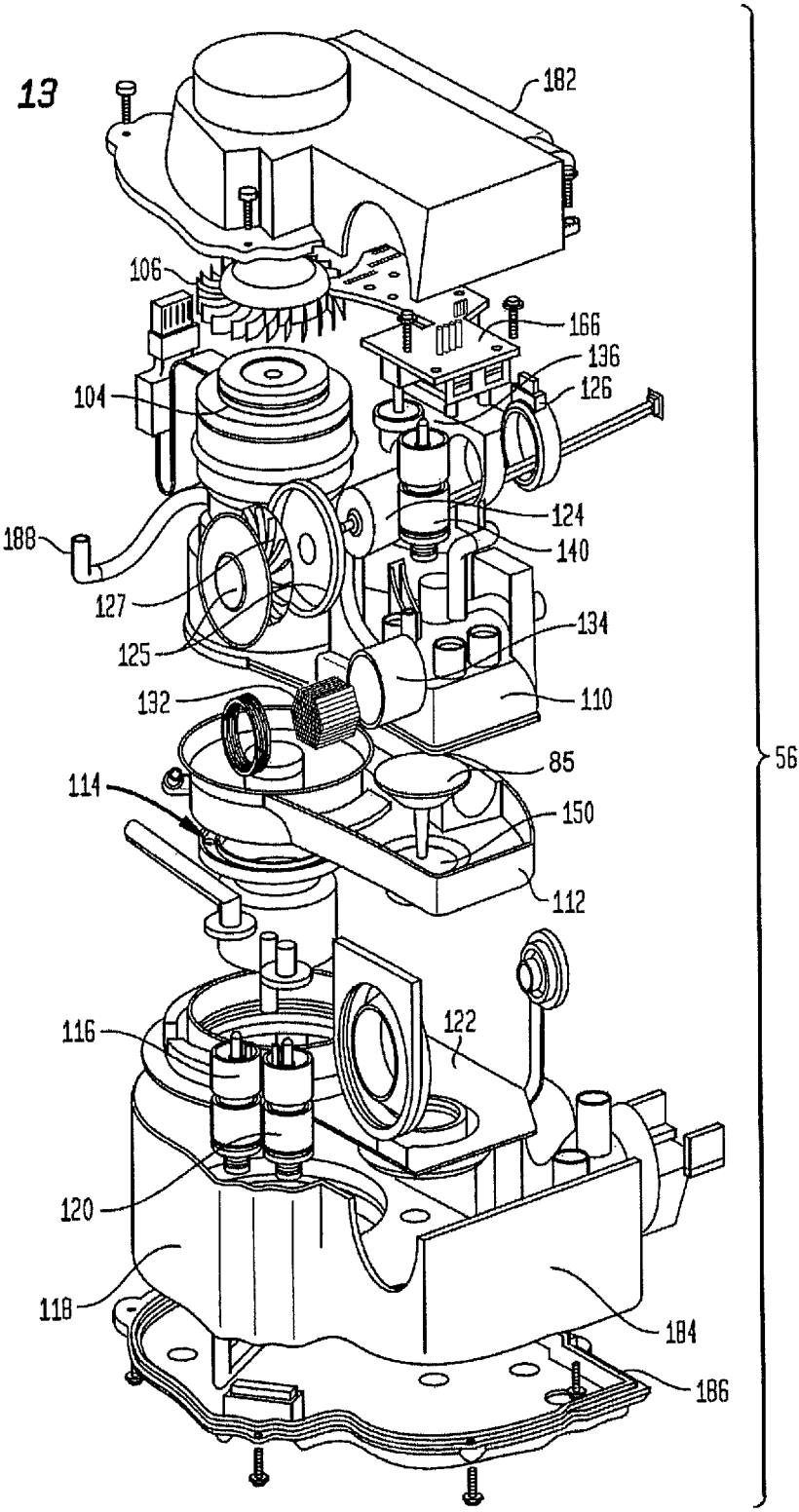
FIG. 13 is an exploded perspective view of a pneumatic block module with components of a volute assembly.

As shown in FIGS. 13, 14 and 15, the pneumatic block module 56 may include a substantially rigid outer casing and may be formed of heat conducting material for good thermal conductivity. For example, it may be formed of aluminum alloy, magnesium, or other material suitable for providing a structural support housing for the module as well as heat conductivity. The outer casing may be formed of metal such as die cast aluminum. The housing may be formed in multiple parts, for example three parts: a main chassis 184, a bottom lid 186 and a top lid 182. The rigid outer casing provides a structural housing for the air path or passages, blower, electronics and other components of the pneumatic block module 56. A seal may be coupled to one or more of the casing parts to form a pneumatic seal around the outer perimeter of the pneumatic block module 56. For example, the bottom lid 186 may include an overmoulded silicone seal around its perimeter. The pneumatic block module contains a substantial portion of the air passages within the ventilator 10 and may be replaced for ease of servicing.

In this regard, the particular design features of the pneumatic block and/or the ventilator housing, such as for example, any one or more of the en-cased structure of the block that is separable/removable from a compartment in the ventilator housing, the number of integrated air passages within the block and/or the integrated calibration record within the block (e.g., a memory or other data storage circuit containing calibration parameter data for operation of the blower that may be accessible by the controller of the blower such as through a cable coupler or electronics interface shown in FIG. 13 coupled to the main blower 104), permit the pneumatic block to more easily serve as a replaceable component of a ventilator when compared to typical ventilator designs. In typical ventilator designs, the blower components are usually jumbled within the ventilator housing and/or require a number of confusing hose connections so as to prevent a simple replacement of the internal components. Thus, the ventilator as a whole must typically be replaced for servicing. Accordingly, the modularized pneumatic block of the present technology permits different servicing methodologies not previously possible. For example, such a modularized pneumatic block may be removed and replaced by a different but similarly structured pneumatic block. In such as case, the ventilator may continue to be used during the servicing of the removed pneumatic block if the removed block is serviced. In this regard, the removed pneumatic block may be separately serviced such as by cleaning and/or calibrating the operational parameters of its components. The removed pneumatic block may then be returned to service such as by replacement back into the ventilator housing it was removed from or another similarly designed ventilator housing. In some cases, the removal may be performed in the field such as at a patient environment (e.g., a home, hospital or clinic). The cleaning (e.g., sterilization) and/or calibration of the removed pneumatic block may then be performed later at a factory or by a repair or servicing centre while the ventilator remains operational in the field. In some cases, it may even be serviced in the field. The modularized design can even permit such service providers to stock a pool of replacement or temporary use pneumatic blocks rather than a pool of ventilators, which may decrease costs. In some cases, the replacement pneumatic blocks may be pre-calibrated in a service centre for the later field insertion into a ventilator. The pneumatic blocks may even serve as replacement components when the ventilator needs a new one or the useful life of the block has been reached.

Figure 12:
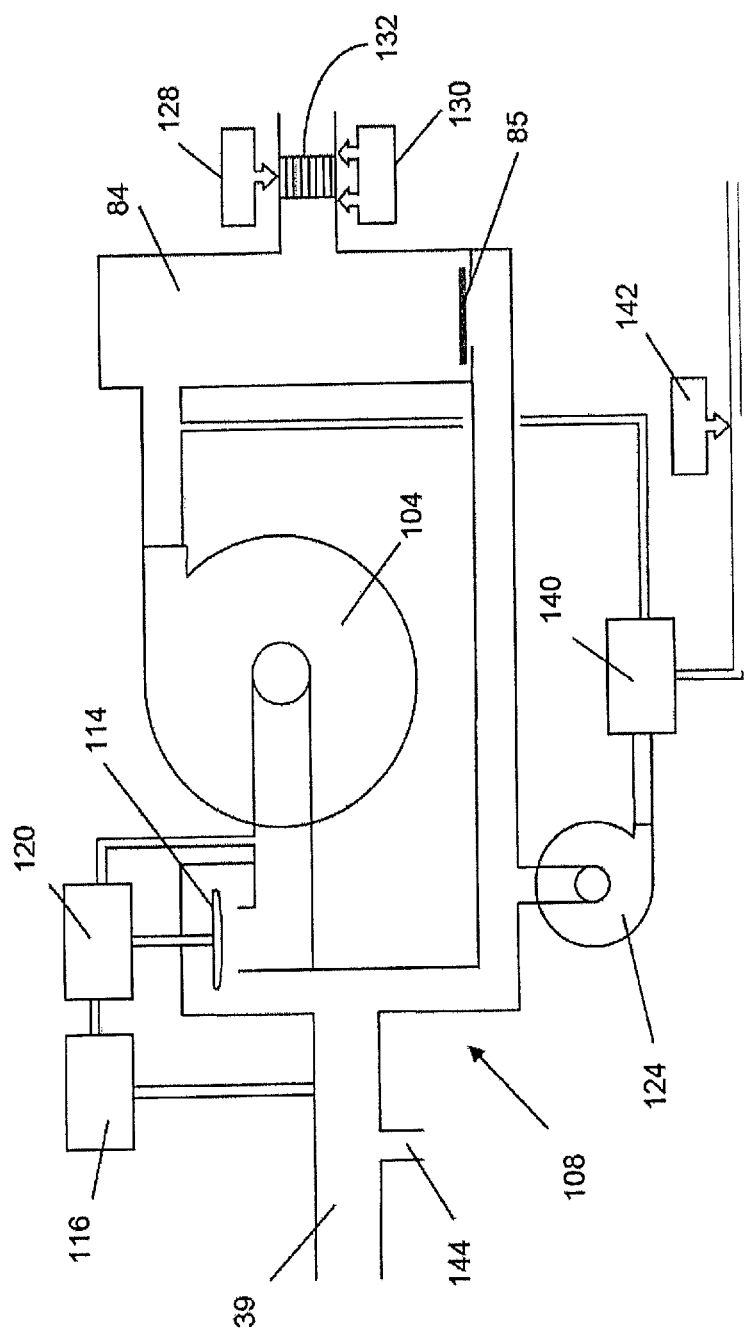
FIG. 12 is a schematic view of the internals of the pneumatic block module according to an example of the disclosed technology.

FIG. 12 is a schematic of the internal components of the pneumatic block module 56. The pneumatic block module 56 includes the main blower 104 with volute assembly 108, an inlet non-return valve assembly 114, an optional oxygen inlet port 144, a positive end expiratory pressure (PEEP) blower or PEEP blower 124, outlet muffler 84, safety valve 85, pressure sensor 128, flow sensor 130 and flow element 132 and a PEEP pressure sensor 142. The volute assembly 108 forms the majority of the airpath and performs some of the critical functions of the pneumatic block module 56.

The sidewalls of the main chassis 184 include openings for the wires of the electrical connections, the expiratory pressure or PEEP pressure tube 188, and for air passages associated with the oxygen supply. A deformable plastic grommet may be configured to fit in the openings of the casing sidewalls to shield the connection wires from potentially sharp edges on the metal openings and provide a seal between the inside and outside of the main chassis 184.

FIG. 13 shows an exploded view of the pneumatic block module 56 and the components therein. The bottom lid 186 is sealingly coupled to the main chassis 184 to form the lower outer surface of the pneumatic block module 56. The main chassis 184 may include electrovalve interfaces 118 to support the pressure release electrovalve 116 and the flow control electrovalve 120 that are configure to communicate with and control the non-return valve assembly 114.

Figure 16A:
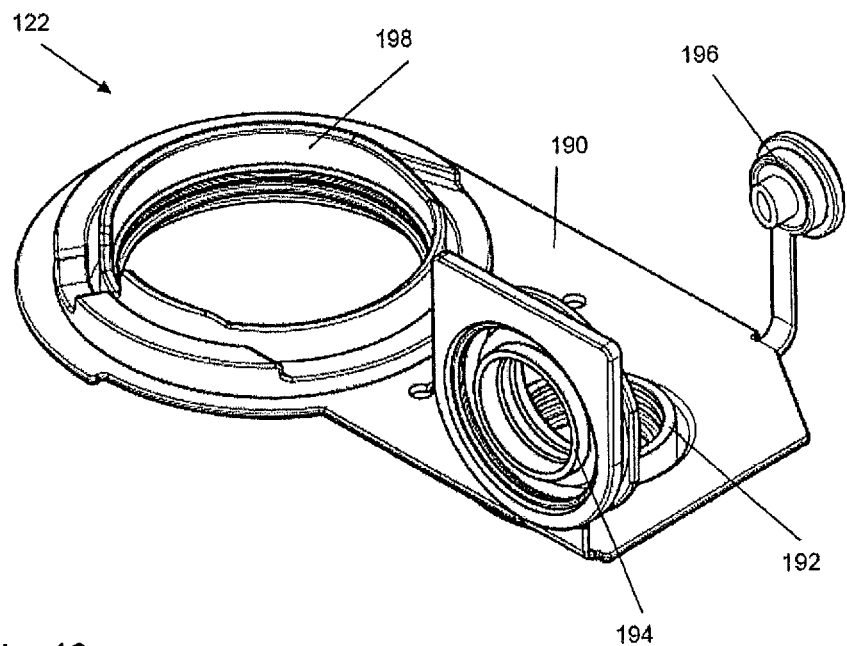
FIGS. 16a and 16b are top and bottom perspective views of a main seal according to an example of the disclosed technology.
Figure 16B:
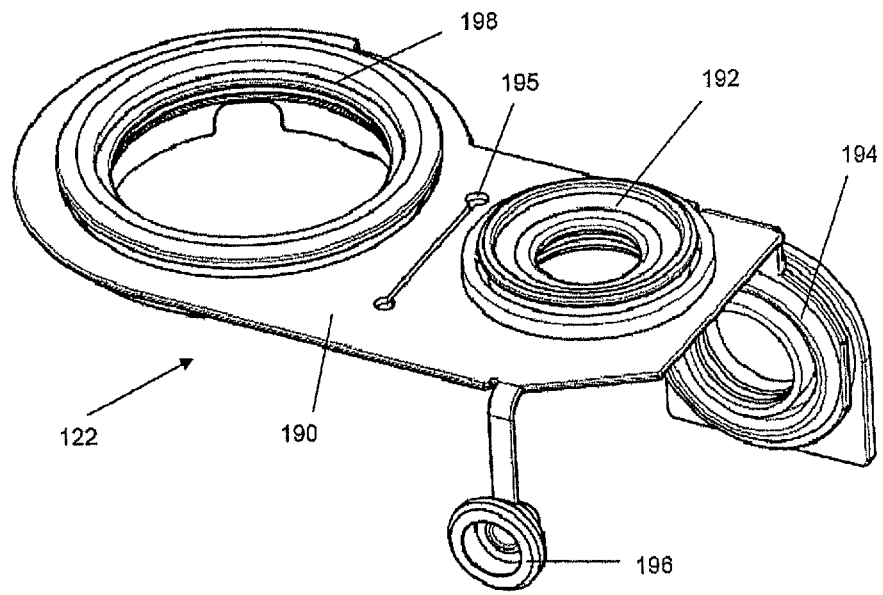
Figure 18A:
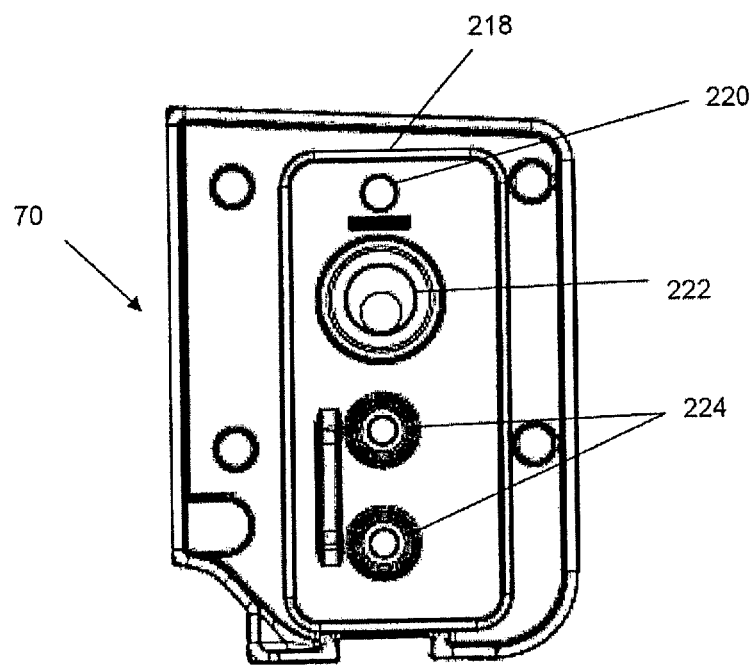
FIGS. 18a to 18d are top, top perspective, side and front views of an expiratory seal according to an example of the disclosed technology.
Figure 18B:
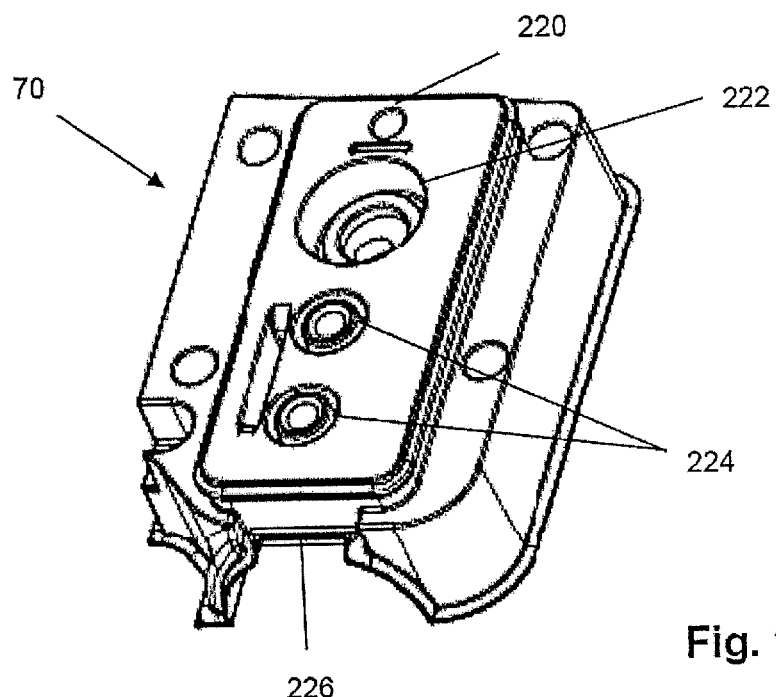
Figure 18C:
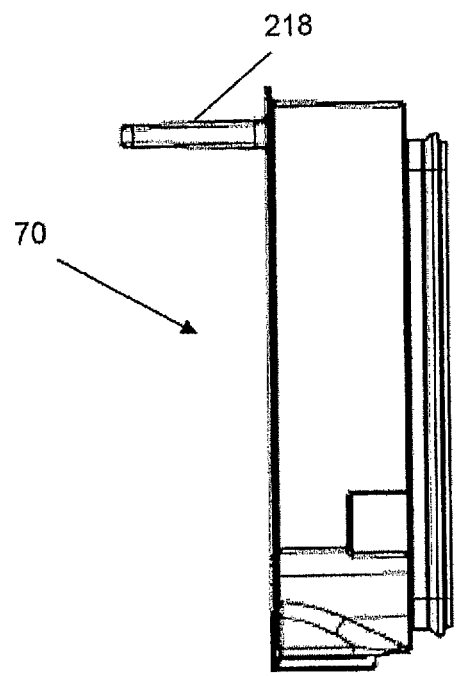
Figure 18D:
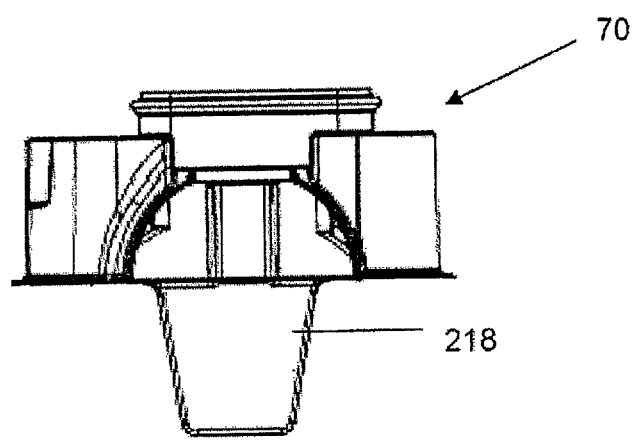
Figure 19A:
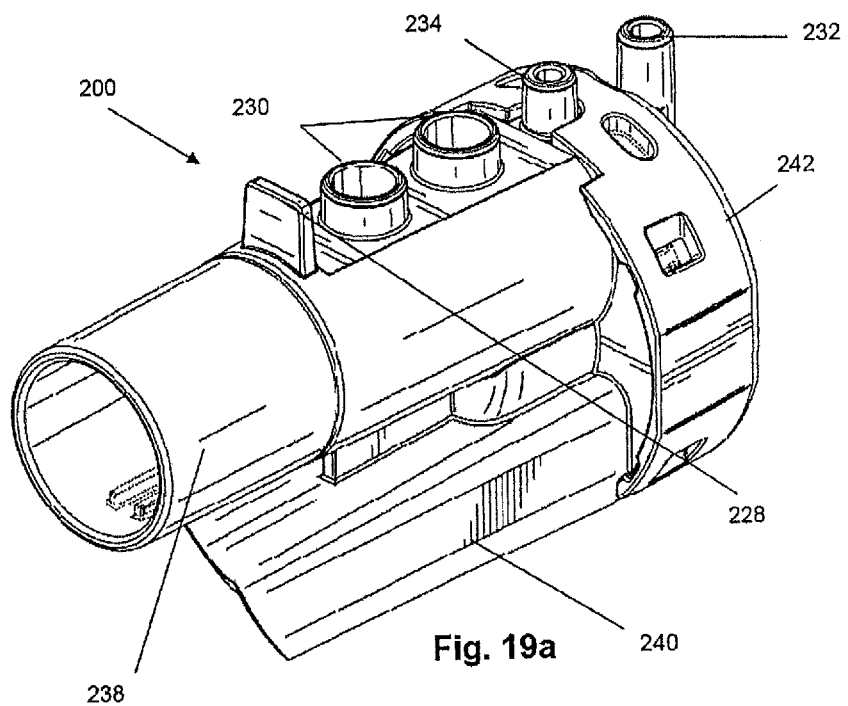
FIGS. 19a to 19d are front perspective, front, back and back perspective views respectively of an expiratory valve according to an example of the disclosed technology.
Figure 19B:
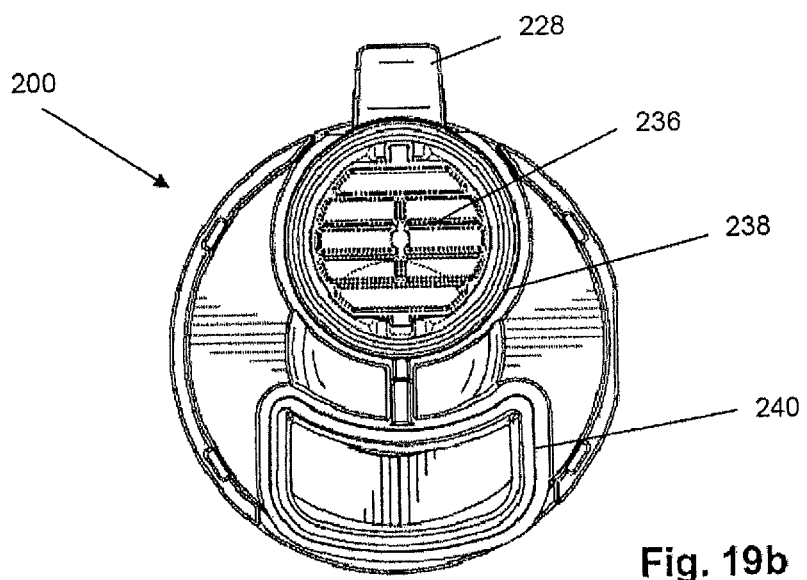
Figure 19C:
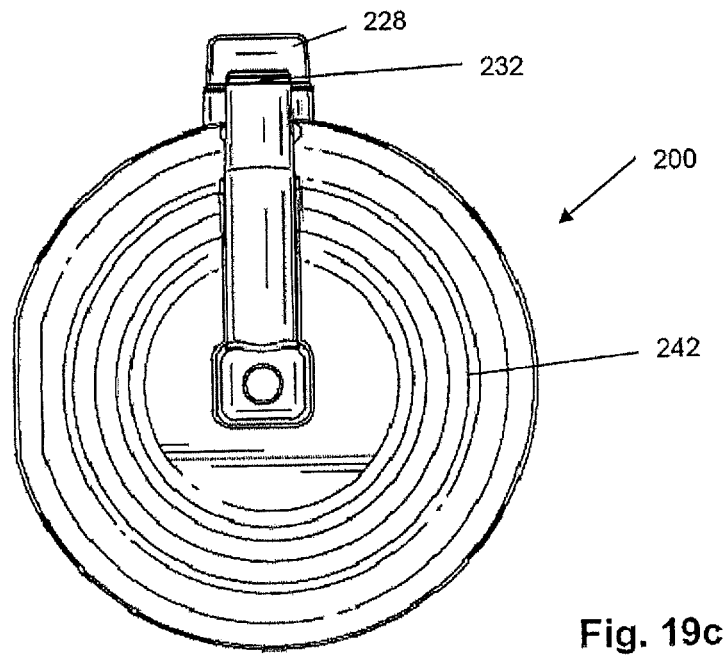
Figure 19D:
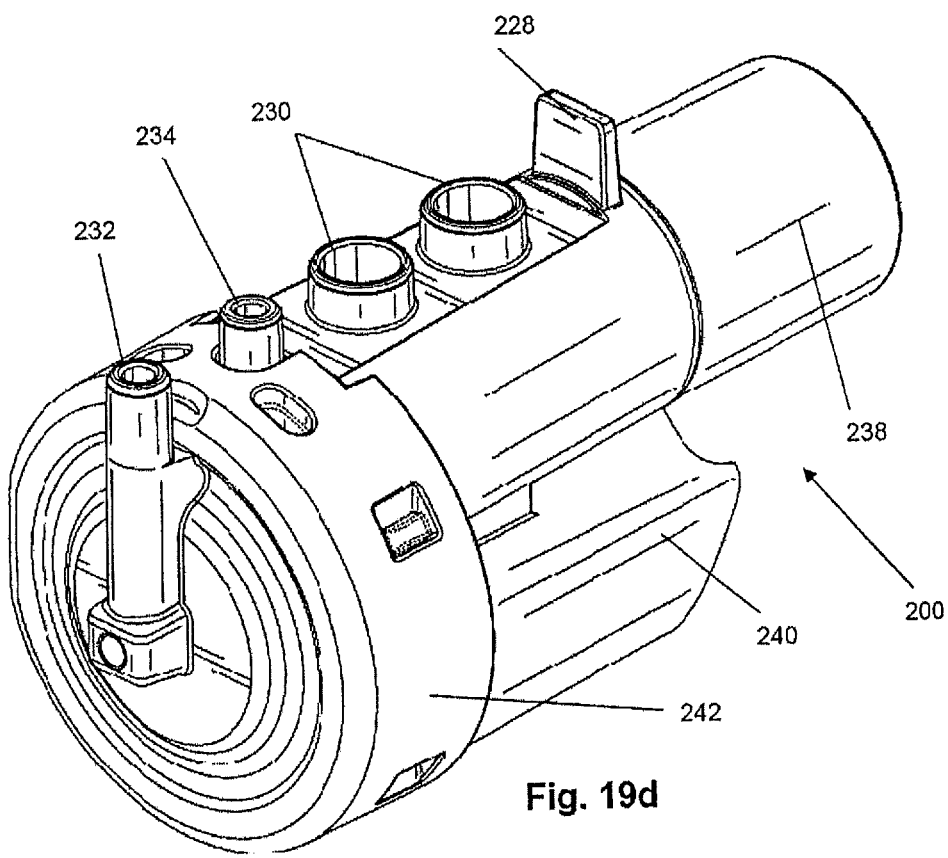

A main seal 122 (which is also shown in FIG. 16) is coupled to the main chassis 184, the main seal 122 provides a surface 190 to join multiple seals between the main chassis 184 and the volute assembly 108 (upper volute 110 and lower volute 112) whilst also providing suspension and/or vibration isolation for the main blower 104. A seal slit 195 may be present within surface 190 to accommodate tolerance variations between the volute assembly 108, pneumatic block main chassis 184 and main seal 122 and to ensure that the sealing areas are not deformed. The seals 198 and 192 together provide the seal between the low pressure inlet side of the main blower and high pressure outlet side of the main blower. The air flow 35 and oxygen flow 45, if present, are mixed within the low pressure inlet side. A sealed inlet chamber is formed between main seal and a seal on the bottom lid 186. As seen in FIGS. 16a and 16b, the main seal 122 may also provide one or more of the following sealing features: to provide the safety valve sealing interface using seal 192 between the safety valve 85 and the aperture in the lower or bottom lid 186 to atmosphere for the safety valve; and to provide the volute outlet sealing interface 194 for the volute outlet 134. The main seal 122 may also provide a volute grommet 196 that is configured to couple to the rear volute support 152 on the volute assembly 108 to help support the volute within the pneumatic block module 56.

The non-return valve assembly 114 comprises a membrane NRVM that is retained to the NRV chamber using a clamping ring. The non-return valve assembly 114 is assembled in the lower volute 112 and is located adjacent the inlet to the main blower 104 to control the level of flow at the blower inlet. The non-return valve may include the non-return valve system as described in the co-owned pending PCT application PCT/AU2011/000341 filed 25 Mar. 2011 which is incorporated by reference herein in its entirety.

The main blower 104 is retained and sealed by the volute assembly. Any form of blower that may provide the required pressures and flow required for ventilation may be utilized, for example a single stage blower or a multistage blower. A blower as described in PCT application PCT/EP2010/066498 filed 29 Oct. 2010 and published as WO 2011/051462 may be used and is incorporated herein by reference in its entirety. A blower suspension 106 is provided above the main blower to provide vibration isolation and/or support to the main blower 104. The blower suspension 106 may also act as a heat sink to facilitate the conduction of heat away from the main blower and to the top lid 182. In such a case, the blower suspension may be formed of a conductive elastomer. The top lid 182 may be formed of a heating conducting material to facilitate the release of the heat away from the main blower 104.

A PEEP blower 124 includes a PEEP impeller 127 and PEEP volute 125 and is configured to provide a pressure source during expiration as required to an expiratory valve 200 (described in more detail below with reference to FIGS. 21 and 22) when located within the compartment of the expiratory portion 31. The PEEP blower 124 is supported by a PEEP suspension 126. The PEEP suspension may be formed of a compliant material to provide vibration isolation and to allow cooling around the PEEP blower 124, for example the PEEP suspension 126 may be formed of silicone, preferably moulded silicone. A PEEP electrovalve 140 controls the supply of the pressure from the PEEP blower 124 to the expiratory portion 31. A PEEP pressure tube 188 is coupled between the PEEP electrovalve 140 and the PEEP supply port 172 (shown in FIG. 5a) in the expiratory portion 31 to provide the PEEP pressure source.

A sensor PCB 166 comprising sensors, such as pressure and/or flow sensors, is coupled via a sensor seal 136 to the upper volute 110 to provide the sensor signals, such as pressure and/or flow signals, for the gas flow as it exits the volute outlet 134.

As seen in FIGS. 14 and 15 the volute assembly 108 may be assembled from one or more moulded components, such as an a upper volute 110 portion and a lower volute 112 portion that are coupled together. The volute assembly 108 may include a plurality of interfaces to provide ease of assembly of the different pneumatic connections required within the pneumatic block module 56. As seen in the upper view, the volute includes the main blower volute 158 that is adapted to receive the main blower 104 and provides the volute area around the main blower 104 (not shown) and the main airpath between the main blower 104 and the volute outlet 134. The volute may also include a PEEP blower support 162, PEEP electrovalve support 160, pressure sensor ports 154, flow sensor ports 156 and the volute outlet 134. The volute outlet 134 may comprise a flow element 132 (not shown in FIG. 14) to facilitate measuring the flow exiting the volute assembly 108. Expired gas flow is routed through the flow element 132 for measuring a differential pressure across the flow element 132.

As seen in FIG. 15, the volute may include a non-return valve (NRV) chamber 146 that is adapted to receive a non-return valve assembly 114 (not shown in FIG. 15). A NRV pressure connector tube 148 is configured to conduct pressure to the NRV chamber 146. The outlet muffler 84 and a safety valve support 150 may also be formed in the volute.

The volute assembly 108 is assembled to the chassis of the pneumatic block module 56 using supports such as the rear volute support 152. A sensor PCB 166 may be coupled to the volute assembly 108 via one or more PCB screw bosses 164.

Air flows through the volute assembly 108 from the inlet muffler through the NRV chamber 146, past the NRV membrane (labeled as "NRVM" in FIG. 13) and into the main blower. After the main blower, the air passes along the volute and down into the outlet muffler which may be formed within the volute. The safety valve 85 is located at the safety valve support 150 within the outlet muffler 84. The air then passes through the flow element 132 and out of the volute outlet 134.

FIGS. 17a to 17c show an embodiment of the sensor seal 136. The sensor seal 136 is configured to be coupled between components on the volute assembly 108, such as the sensor ports and electro valve port, and to integrated sensors of the sensor PCB 166. The sensor seal 136 is formed of a compliant material such as silicone and provides sealing connections between sensors on the PCB and the components on the volute assembly 108 and from the PEEP blower 124 to the PEEP electrovalve 140. The sensor seal 136 may also serve to mount the sensor PCB 166 to the volute assembly 108. The sensor seal 136 may also protect the sensor PCB 166 against shocks and vibration.

By fitting the sensor PCB 166 having multiple sensors to the sensor seal 136 having multiple port seals, the connections between the pressure sensors and the air passages in the volute assembly are quickly and reliably formed. Furthermore, the sensor PCB 166 and the arrangement of pressure sensors thereon may allow for a unique mounting orientation onto the sensor seal 136 which may minimize the risk of pressure sensors not being properly connected to the air passages in the volute assembly 108.

The sensor seal 136 includes a first side 136a as shown in FIG. 17a that is configured to engage with the pressure sensor ports 154, flow sensor ports 156 and the PEEP electrovalve 140 within the PEEP electrovalve support 160 on the volute. A second side 136b, as shown in FIG. 17c, is configured to engage with sensors located on the sensor PCB 166. The first side 136a includes two flow element bypass ports 214, an entry port and an exit port that are connected to the flow sensor ports 156 on the volute. On the second side 136b of the sensor seal 136 the two flow element bypass ports 214 are coupled to the flow element on the sensor PCB 166 to allow a bypass flow of the outlet gas flow to be measured to provide a flow signal for the outlet gas flow.

The first side 136a also includes an outlet pressure port 210 and an inspiratory/expiratory pressure port 204 that are engaged with the pressure sensor ports 154 in the volute. The second side 136b provides an outlet pressure sensor seal 206 and an inspiratory/expiratory pressure sensor seal 212 that are configured to pneumatically engage with the outlet pressure sensor and the inspiratory/expiratory pressure sensor located on the sensor PCB 166 to allow pressure measurements of the outlet gas flow and the expired gas flow respectively. The sensor PCB may also be secured to the volute assembly 108 by fasteners, e.g., screws.

A PEEP electrovalve port 216 is also located on the first side 136a of the sensor seal 136 and is configured to engage with the PEEP electrovalve 140 that is located within the PEEP electrovalve support 160 on the volute. The second side 136b of the sensor seal includes a PEEP pressure port 208 configured to connect to an outlet of the PEEP blower 124, thus in use the PEEP pressure port 208 is configured to provide a PEEP pressure supply to the PEEP electrovalve 140 for controlling the expiratory valve 200.

By housing the majority of the air passages and pneumatic connections within the outer casing of the pneumatic block module 56, the number of air tubes exposed outside of the casing is minimized. Housing the pneumatic connections within the casing reduces any risk that tubes become disconnected, leak or are incorrectly connected to air passages. Further, housing the pneumatic connections in the casing of the pneumatic block reduces the complexity of the components within the housing, in that some of the complexity from the pneumatic connections may be confined to the pneumatic block module 56.

To replace the complete air passage within the ventilator 10 the filter assembly 36, inlet seal 38, pneumatic block module 56, inspiration outlet port 16 and the components of the expiratory portion 31 are disconnected and/or unplugged from the housing and replaced. In the expiratory portion 31 one or more of the following components may be replaced: expiratory valve 200, expiratory adaptor 202, expiratory seal 70, sensor filter, and flow element. There is no requirement to disconnect and then reconnect a plurality of tubes to make the pneumatic connections within the ventilator as the majority of such pneumatic connections are formed within the replaceable pneumatic block module 56. For the replacement of the air path a new filter assembly 36 is inserted into the inlet filter support 176 and a new inlet seal 38 is coupled to the inlet seal support 178. A new pneumatic block module 56 is attached to the housing 12, and coupled to the inlet seal 38 at the pneumatic block module inlet and to a new inspiration outlet port 16 at the pneumatic block module outlet. A new expiratory seal 70 (discussed with reference to FIG. 18), sensor filter, flow element and expiratory valve 200 or expiratory adaptor 202 may be inserted into the expiratory portion 31. Several air passage connections are formed by inserting the pneumatic block module into the housing. The additional air passage connections needed to be made after the module is in place in the housing may be relatively few. For example the PEEP pressure tube 188 is attached to expiratory portion 31. Consolidating the air passages in the pneumatic block module avoids the complicated nest of tubes and other air passages found in conventional ventilators.

Expiratory Portion 31

The expiratory portion 31 is adapted to receive the expired gas 55 from the patient. The expiratory portion may be configured as a compartment to receive a removable expiratory interface module, such as an expiratory valve 200 or expiratory adaptor 202 that may serve to route expiratory gas for various purposes. As described above the chassis 21 includes some interfaces to receive a sensor filter and expiratory flow sensor. An expiratory cover 48 for the compartment of the expiratory interface module is a separable part of the housing 12. The expiratory cover 48 may include a release button 50R and latch dial 50L (see FIG. 4) which may be operated by hand to allow the cover to slide off from the housing. After the expiratory cover 48 is removed, the expiratory interface module may be lifted out of the housing. The compartment of the expiratory portion 31 may also be configured to receive an expiratory seal 70 that conforms to an internal surface shape of the compartment. The seal may be adapted to retain and seal an expiratory sensor filter, an expiratory flow sensor and provide air ports to connect to the expiratory gas routing modules (e.g., expiratory adapter and expiratory valve), to the air passages in the housing 12 The expiratory seal 70 is deformable and provides a structural support for the expiratory interface module and may shield the module from shocks and vibrations and also assist in minimizing the entry of dirt and contamination to the sensors and ports within the expiratory portion 31.

FIGS. 18a to 18d show an example expiratory seal 70. The expiratory seal 70 is adapted to be inserted into the compartment of the expiratory portion 31 and forms a sealing interface between the gas ports interface of the chassis of the housing 12 and the expiratory gas routing module. In the example, the gas routing module may be inserted into the expiratory portion 31 and form a sealed interference fit with the seal and the gas ports interface of the compartment. An optional tab 218 may be provided on the expiratory seal 70 to facilitate ease of removal of the expiratory seal 70 by pulling the tab 218 to pull out the expiratory seal 70. Preferably the expiratory seal 70 has an irregular or unique outer shape to facilitate proper alignment for insertion into the expiratory portion 31. Optionally, an aperture 226 may be formed between the expiratory seal 70 and the chassis 21 within the expiratory portion 31 to form an alignment feature for insertion of the expiratory interface module (e.g., expiratory valve 200 or expiratory adapter 202).

The expiratory seal 70 may provide a plurality of sealed pneumatic channels, such as a PEEP supply channel 220, an expiratory pressure sensor channel 222 and a pair of expiratory flow sensor channels 224. The PEEP supply channel 220 is configured to connect between the PEEP supply port 172 formed in the expiratory portion 31 of the chassis 21 and the PEEP supply port on the expiratory interface module (e.g., expiratory valve 200 or expiratory adapter 202). The PEEP supply channel provides a route for the PEEP gas flow. By seating the expiratory interface module on the expiratory seal 70 in its unique aligned position, the air passages for the module are properly aligned with the air passages, sensors and filters in the ventilator.

An expiratory flow sensor and a sensor filter for a pressure sensor sit within an expiratory portion compartment of the chassis. In this regard, the expiratory flow sensor interface 170 and sensor filter interface 168 in the chassis 21 are shown in FIG. 5a. The expiratory seal 70 is seated over the flow sensor and sensor filter. The expiratory pressure sensor channel 222 forms a channel between the sensor filter and a pressure port on the expiratory interface module. The pair of expiratory flow sensor channels 224 provides a bypass flow between a flow element that is located within the expiratory interface module for measuring the expiratory flow rate. The pair of expiratory flow sensor channels 224 are connected between a flow sensor and flow ports on an expiratory interface module. Thus, the channels 222, 224 provide conduits connecting the air passages in the expiratory interface module (e.g., expiratory valve 200) with sensors in the housing 12.

FIGS. 19a to 19d and FIGS. 20a to 20c show an example expiratory valve 200 that is adapted as an expiratory interface module to be seated on the expiratory seal within the expiratory compartment. FIGS. 21a to 21d and FIGS. 22a to 22c show an example expiratory adaptor 202 that is alternatively adapted to be seated on the expiratory seal within the expiratory compartment.

The expiratory valve 200, as seen in FIGS. 19a to 19d, may include an expired gas inlet 238 adapted to be connected to an air delivery conduit (not shown) to receive gas expired by the patient. The expired gas passes through the expiratory valve 200 and exits to atmosphere through an expired gas outlet port 240. The expiratory valve 200 may comprise at least one alignment tab 228 to assist with correctly aligning and retaining the expiratory valve to the expiratory seal 70. The alignment tab 228 may be received within the aperture 226 created between the chassis 21 and the expiratory seal 70 when the expiratory seal is inserted into the chassis 21.

The expiratory valve 200 comprises a PEEP pressure port 232, pressure sensor port 234 and a pair of flow sensor ports 230 that are aligned with the PEEP supply channel 220, expiratory pressure sensor channel, and expiratory flow sensor channels in the expiratory seal 70 when the expiratory valve 200 is seated on the expiratory seal 70. An expiratory flow element 236 may be located within the expired gas inlet 238 in an expiratory airflow path or channel between the pair of flow sensor ports 230 and within the expiratory valve. The flow sensor ports 230 allow a flow sensor to detect the flow rate of the expired gas from the patient. Similarly, the pressure sensor port 234 that connects with an internal channel of the expiratory valve allows the pressure of the expired gas to be sensed by a pressure sensor. The PEEP pressure port 232 is configured to receive a supply of pressurized gas from the PEEP blower 124 and channel the gas within the expiratory valve, the flow of which is used to control the operation of a PEEP membrane located within a removable valve cap 242 of the expiratory valve 200.

The expiratory valve 200 may be inserted into the expiratory compartment so that the ventilator may serve as a dual limb ventilation system, i.e. separate inspiratory and expiratory gas delivery conduits are used. In such a case, an inspiratory gas supply generated by the ventilator 10 is delivered to a patient interface device via an inspiratory gas conduit that is coupled to the inspiration outlet port 16. The patient expired gas is delivered back to the expiratory portion 31 of the ventilator 10 via an expiratory gas conduit. The expiratory valve 200 together with the PEEP blower 124 are adapted to regulate a positive end expiratory pressure during expiration.

Figure 20A:
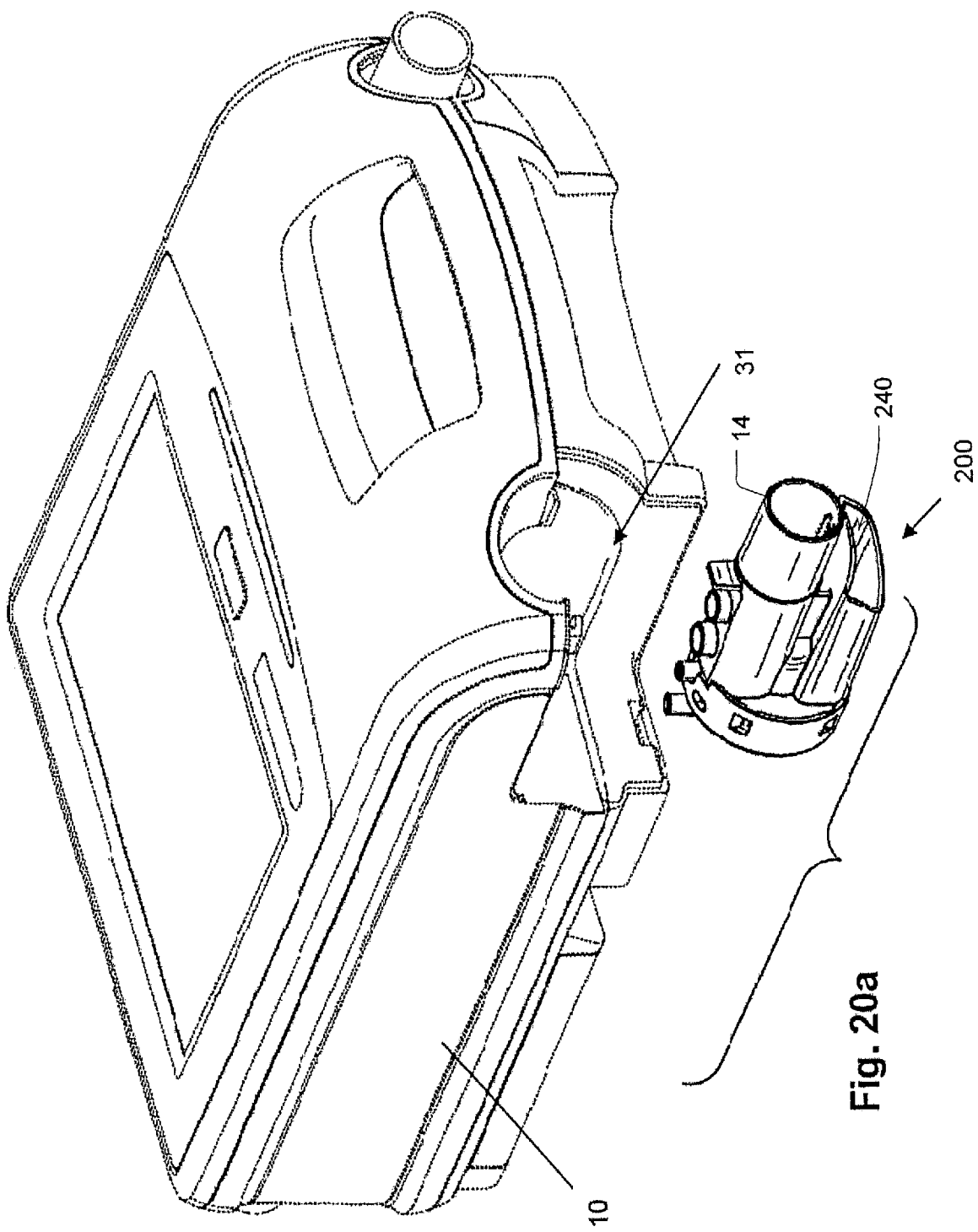
FIGS. 20a to 20c indicate how the expiratory valve of FIGS. 19a to 19d may be coupled to a ventilator according to an example of the disclosed technology.
Figure 20B:
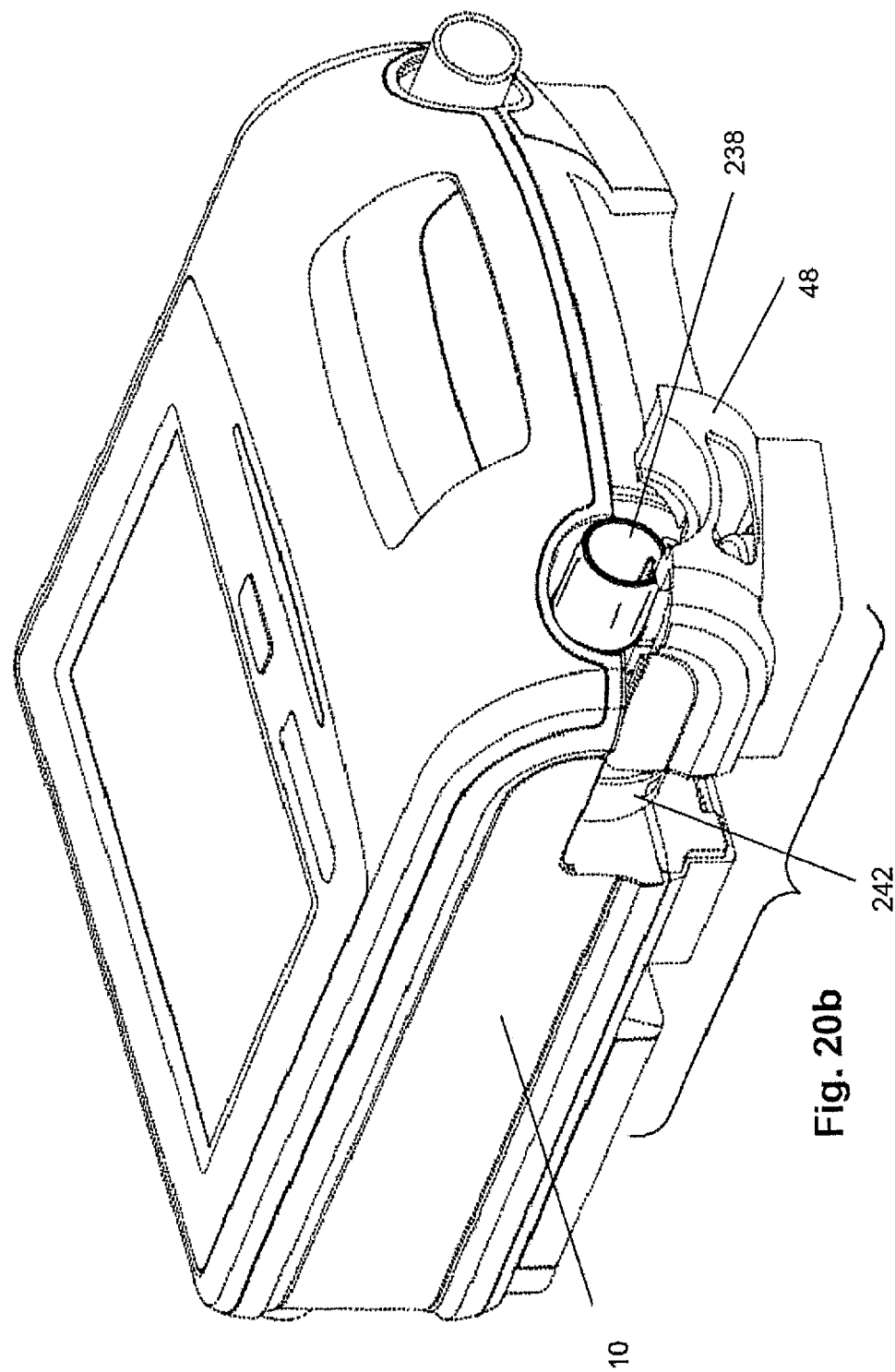
Figure 20C:
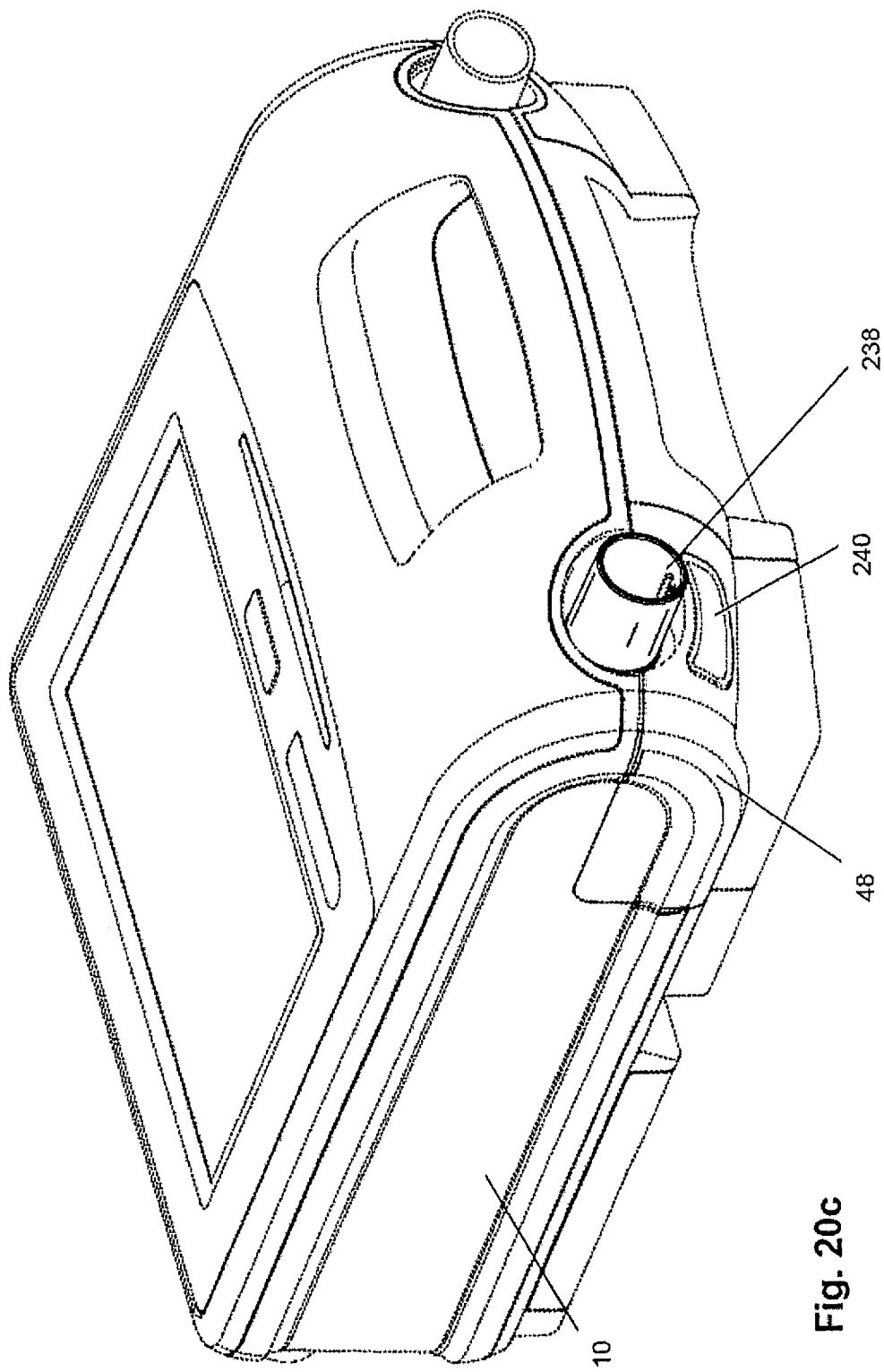
Figure 21A:
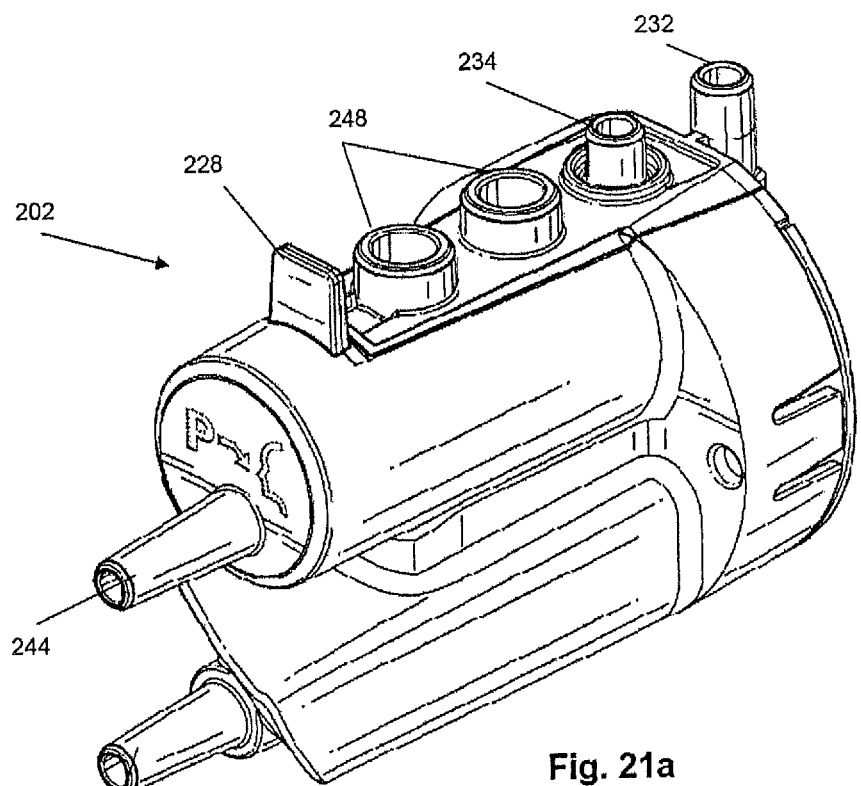
FIGS. 21a to 21d are front perspective, front, back and back perspective views respectively of an expiratory adaptor according to an example of the disclosed technology.
Figure 21B:
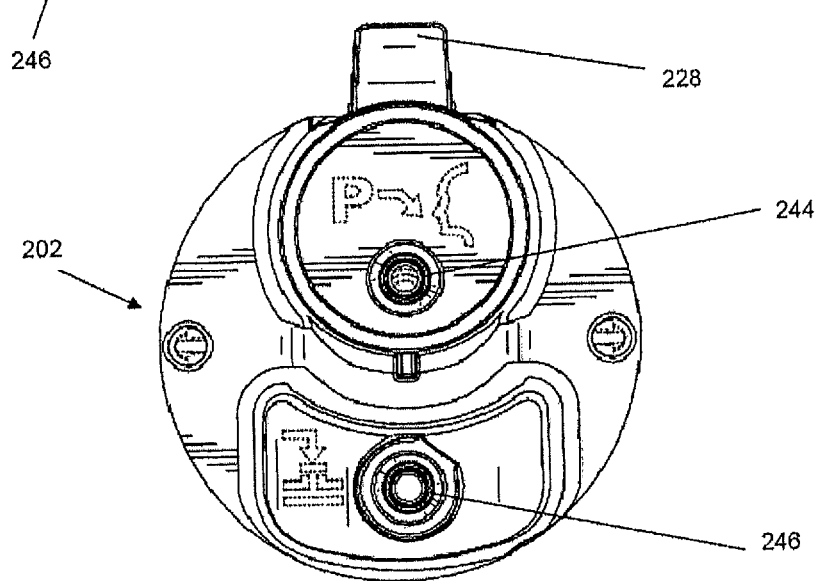
Figure 21C:
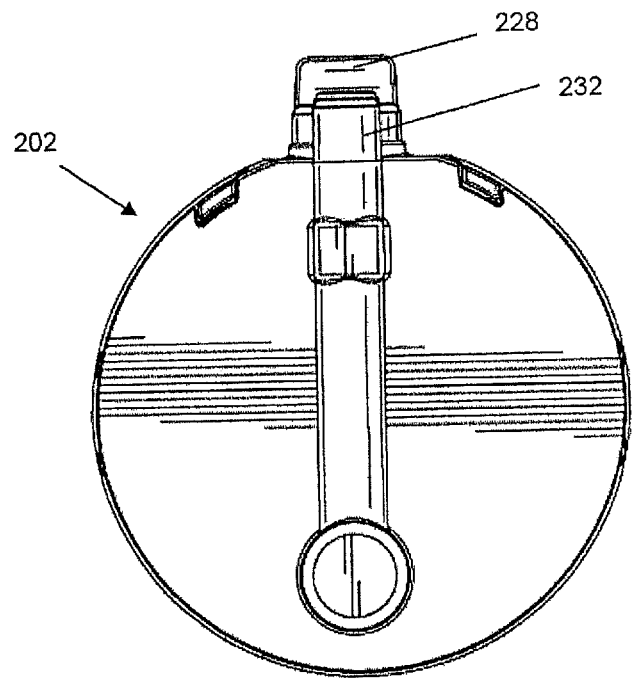
Figure 21D:
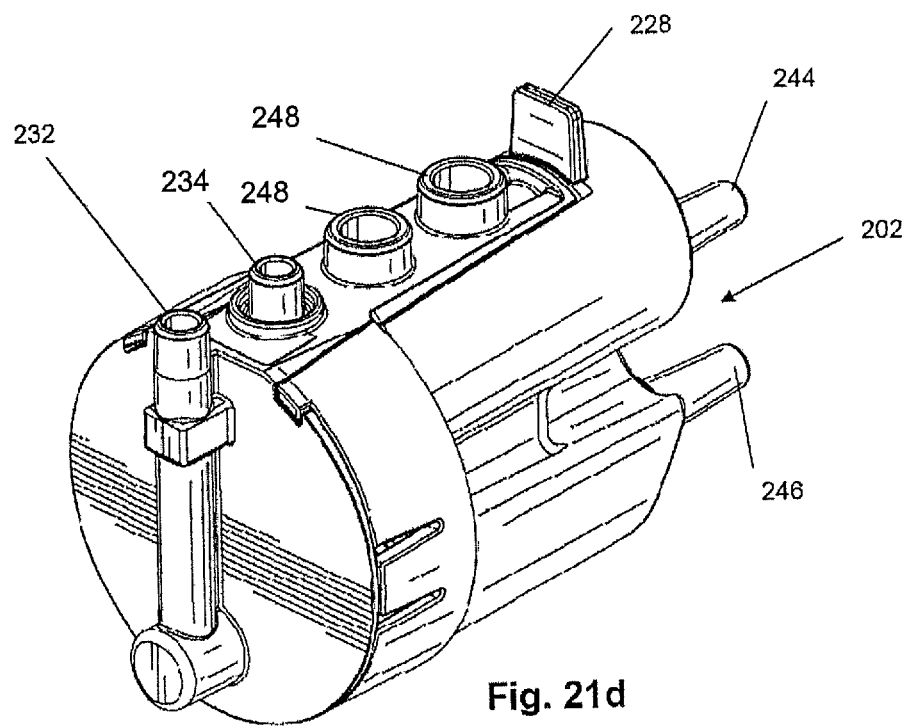

FIGS. 20a to 20c illustrate insertion of the expiratory valve 200 into the expiratory portion 31 of the ventilator 10 and the insertion of the expiratory cover 48 to retain the expiratory valve 200 within the compartment of the expiratory portion 31 of the ventilator 10.

FIGS. 21a to 21d show an example of an expiratory adaptor 202 that is configured to be seated on the expiratory seal 70 within the compartment of the expiratory portion 31 of the ventilator 10. The expiratory adaptor has a complementary interface configuration to that of the expiratory valve 200 to facilitate insertion within the same compartment and same seal despite serving, in part, a different gas routing purpose. The expiratory adaptor may also comprise at least one alignment tab 228 to assist with correctly aligning and retaining the expiratory adaptor 202 to the expiratory seal 70. The alignment tab 228 may be received within the aperture 226 created between the chassis 21 and the expiratory seal 70 when the expiratory seal is inserted into the chassis 21.

The expiratory adaptor 202 comprises a PEEP pressure port 232 and a pressure sensor port 234 in a similar manner to the expiratory valve 200. However, the expiratory adaptor does not comprise a PEEP membrane for controlling the PEEP pressure as this is provided in a proximal expiratory valve (not shown). The PEEP pressure port 232 routes the PEEP pressure from the PEEP blower 124 to the proximal expiratory valve via a tube that is coupled to an adaptor PEEP control port 246. A pressure measurement of the expired gas is made via delivery of a supply of the expired gas via another small tube connection to an adaptor pressure inlet port 244 that is connected within the expiratory adaptor 202 and routes expired gas to the pressure sensor port 234 for measuring of the pressure at the pressure sensor.

In this embodiment, there is no expiratory flow routed through a flow element within the expiratory adaptor as an expiratory flow measurement is not necessary. Thus, ports 248 may be blank ports (e.g., no connecting channel) that can be used to assist in aligning and retaining the expiratory adaptor 202 in its sealed position with the expiratory seal 70.

Insertion of the expiratory adaptor in the expiratory compartment permits the ventilator to serve as a single limb ventilation system with a proximal expiratory valve. In such a system an inspiratory gas conduit is connected to the inspiration outlet port 16 in a similar manner to that described above for the expiratory valve. However, there is no expiratory gas conduit as a proximal expiratory valve is connected proximal to the patient. The proximal expiratory valve releases the majority of the expired gas 55 at a location proximal to the patient.

As illustrated with respect to FIGS. 23 through 30, a pneumatic coupler 2300 may be adapted to serve as a removable connection for the ports of the ventilator's expiratory adapter 202 and conduits for the patient circuit or patient interface. Such a coupler may be adapted with a configuration to ensure this coupling with the multiple ports of the adapter 202 in only one manner so as to avoid an incorrect connection between the ports and the conduits of the patient circuit.

For example, as illustrated, the coupler 2300 may have a ventilator connection end 2301 and a patient circuit end 2303. The ventilator connection end 2301 of the coupler 2300 may include first and second port connectors 2302-1, 2302-2 and as such, serves as an pneumatic interface to the ventilator from, for example, a single patient circuit with a proximal valve. These ports will include first and second gas channels 2302-1-GC, 2302-2-GC. The first port connector 2302-1 of the coupler 2300 may be configured for coupling only with the adapter pressure inlet port 244 of the expiratory adapter 202, the port that senses patient pressure. The second port connector 2302-2 of the coupler 2300 may be configured for coupling only with the PEEP control port 246 of the expiratory adapter, the port for controlling PEEP pressure. Such a connection between the ventilator connection end 2301 of the coupler 2300 and the expiratory adapter 202 of the ventilator 10 may be, for example, by an interference fit at the ports.

The coupler may also include an alignment protuberant, such as connection ring 2304, to enforce proper alignment of the ports and port connectors. In this regard, the alignment protuberant may be configured for insertion, such as by interference fit, with a structure of the ventilator, such as a receiving channel RC of the housing of the ventilator. The collective structures may be configured to permit the insertion in only one orientation. For example, the connection ring 2304 may be sized and configured for insertion within a receiving channel RC of the expiratory portion 31 (best seen in FIG. 22C). Such an insertion permits the proper alignment and sealing of the ports and port connectors. In this regard, the first port connector may itself be cylindrical and may be located within a portion of the greater circumference of an inner cylindrical chamber 2344 (best seen in FIG. 26) of the connection ring and may be offset from a center of the connection ring (or offset from a central axis of the cylindrical chamber) as illustrated. In this embodiment, the inner cylindrical chamber 2344 itself does not serve as a passage of gas channel for pressure or gas of the respiratory treatment system. The second port connector may also be cylindrical and may be located outside the circumference of the connection ring or otherwise outside the cylindrical chamber. In this way, a single coupler for multiple conduits may be configured for connection in only one alignment orientation so as to only permit a proper connection of multiple ports (e.g., two or more).

The patient circuit end 2303 of the coupler may then have integrated conduits, in proper orientation, such as flexible tubes of the patient circuit that may include the patient interface (not shown). For example, in the illustrated embodiment the conduits may be bonded to the coupler or may otherwise be formed therewith. One or more of these tubes may lead to or connect to a proximal valve (not shown). Such tubes may provide a pneumatic conduit for patient pressure signals (e.g., from a patient mask (not shown)) and pneumatic control pressure to the proximal valve from the ventilator. In the illustrated example embodiment, the expiratory conduit 2306 leads to the adapter pressure inlet port 244 via the first port gas channel 2302-1-GC of the coupler and the PEEP control conduit 2308 leads to the PEEP control port 246 via the second port gas channel 2302-2-GC of the coupler. As illustrated therein, the coupler may serve as a twin connection where each port connection is the same size and shape. For example, the diameter and shape of the two points of contact of the first port connector 2302-1 and the second port connector 2302-1 can be the same. For example, the may both have the same cylindrical connector and gas channel size. Nevertheless, the structural configuration of the coupler, as a whole, including the alignment feature will prevent any confusion concerning which port connector connects to which port of the expiratory adapter. In the case that the patient interface and proximal valve at the opposing end of the conduits 2308, 2306 are not integrated or bonded with the conduits 2308, 2306, though they may be, a multiport coupler design may also be implemented at the opposing end to ensure that the conduits couple to ports of the patient interface and proximal valve properly, (e.g., in only one alignment orientation).

Generally, the coupler 2300 may be formed of an elastomeric material. The elastomeric material may help to provide a sealed connection with the ventilator and the expiratory adaptor). The connector may also be designed to blend with the shape and form of the ventilator housing so as to make the coupled assembly as unobtrusive as possible. For example, the connection ring 2304 may be a cylindrical structure that is chamfered on one curved end CE so when it is properly inserted it has a surface that conforms (e.g., the surfaces may be approximately flush) to an exterior surface of the ventilator housing profile. Similarly, a coupler bend CB may be implemented to maintain the conduits in a close proximity to the housing. In this regard, the bend may serve to direct the gas channels of the coupler at an angle (e.g., a 45 degree bend, 90 degree bend, etc.).

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

It will further be understood that any reference herein to known prior art does not, unless the contrary indication appears, constitute an admission that such prior art is commonly known by those skilled in the art to which the invention relates.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to invasive and non-invasive ventilation, it is to be appreciated that patients who suffer from a variety of respiratory related conditions or illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A gas routing module for insertion within a respiratory treatment apparatus, the gas routing module adapted to couple within a gas ports interface of a discrete compartment of a chassis of a respiratory treatment apparatus, the gas routing module comprising:
    a plurality of gas routing channels adapted for gas communication with expired airflow; and
    a gas ports interface, the gas ports interface including a plurality of gas ports in gas communication with the plurality of gas routing channels,
    wherein the gas ports interface of the gas routing module comprises two or more of (a) a port for expiratory pressure sensing, (b) a port for a positive end expiratory pressure (PEEP) air supply, and (c) a set of ports for expiratory flow sensing through one or more of the plurality of gas routing channels of the module,
    wherein the gas routing module has a first side including (1) an expired gas inlet port adapted to be connected to a conduit of a patient circuit, and (2) a gas outlet port,
    wherein, in use, the expired gas inlet port receives, at the first side, the expired airflow from the conduit of the patient circuit, and the gas outlet port exhausts, at the first side, from the respiratory treatment apparatus, one of (a) a PEEP supply gas from a PEEP blower, and (b) expired airflow from the conduit of the patient circuit.

2. The gas routing module of claim 1, further comprising a flow element, wherein a gas routing channel of the plurality of gas routing channels is configured to route an expired air flow through the flow element for measuring differential pressure across the flow element.

3. The gas routing module of claim 2, wherein a gas routing channel of the plurality of gas routing channels of the module comprises a PEEP supply channel.

4. The gas routing module of claim 3, wherein the PEEP supply channel comprises a membrane.

5. The gas routing module of claim 4, further comprising a removable cover for accessing the membrane.

6. The gas routing module of claim 1, wherein one of the plurality of gas routing channels of the module comprises an expiratory pressure routing channel for pressure sensing.

7. The gas routing module of claim 1, wherein the gas ports interface of the gas routing module comprises a blank port.

8. The gas routing module of claim 1, wherein the expired gas inlet port is an expiratory pressure sensing inlet port.

9. The gas routing module of claim 1 comprising the port for expiratory pressure sensing, the port for a PEEP air supply, and the set of ports for expiratory flow sensing, wherein the port for expiratory pressure sensing is located on the gas ports interface between the port for the PEEP air supply and the set of ports for expiratory flow sensing.

10. The gas routing module of claim 1 wherein the gas from the respiratory treatment apparatus exhausted from the gas outlet port is the expired airflow from the conduit of the patient circuit.

11. The gas routing module of claim 1 wherein the gas from the respiratory treatment apparatus exhausted from the gas outlet port is a PEEP supply gas from a PEEP blower.

12. The gas routing module of claim 1 wherein the expired gas inlet port of the gas routing module is configured to extend from the discrete compartment to outside of an external housing of the respiratory treatment apparatus.

13. A respiratory treatment apparatus configured to provide a flow of breathable gas to a patient, the respiratory treatment apparatus comprising a blower for providing the flow of breathable gas, a chassis including a gas ports interface in a discrete compartment of the chassis of the respiratory treatment apparatus to receive a gas routing module, and the gas routing module adapted to removeably couple within the gas ports interface,
    the gas routing module comprising:
        a plurality of gas routing channels adapted for gas communication with expired airflow; and
        a gas ports interface, the gas ports interface including a plurality of gas ports in gas communication with the plurality of gas routing channels,
        wherein the gas ports interface of the gas routing module comprises two or more of (a) a port for expiratory pressure sensing, (b) a port for a PEEP air supply, and (c) a set of ports for expiratory flow sensing through one or more of the plurality of gas routing channels of the module,
    wherein the gas routing module has a first side including (1) an expired gas inlet port adapted to be connected to a conduit of a patient circuit, and (2) a gas outlet port,
    wherein, in use, the expired gas inlet port receives, at the first side, the expired airflow from the conduit of the patient circuit, and the gas outlet port exhausts, at the first side, from the respiratory treatment apparatus, one of (a) a PEEP supply gas from a PEEP blower, and (b) expired airflow from the conduit of the patient circuit.

14. The respiratory treatment apparatus as claimed in claim 13, wherein the respiratory treatment apparatus is a ventilator.

15. The respiratory treatment apparatus as claimed in claim 14, wherein the ventilator comprises a removeable cover for the discrete compartment.

16. The respiratory treatment apparatus as claimed in claim 14, wherein the gas routing module further comprises a flow element, wherein a gas routing channel of the plurality of gas routing channels is configured to route the expired airflow through the flow element for measuring differential pressure across the flow element.

17. The respiratory treatment apparatus as claimed in claim 16, wherein a gas routing channel of the plurality of gas routing channels of the module comprises a PEEP supply channel.

18. The respiratory treatment apparatus as claimed in claim 17, wherein the PEEP supply channel comprises a membrane.

19. The respiratory treatment apparatus as claimed in claim 18, wherein the gas routing module further comprises a removable cover for accessing the membrane.

20. The respiratory treatment apparatus as claimed in claim 14, wherein one of the plurality of gas routing channels of the module comprises an expiratory pressure routing channel for pressure sensing.

21. The respiratory treatment apparatus as claimed in claim 14, wherein the gas ports interface of the gas routing module comprises a blank port.

22. The respiratory treatment apparatus as claimed in claim 14, wherein the expired gas inlet port is an expiratory pressure sensing inlet port.

23. The respiratory treatment apparatus of claim 13 wherein the discrete compartment comprises a pneumatic interface that is configured to mate with a plurality of different gas routing modules comprising the gas routing module, the plurality of different gas routing modules comprising (a) an expiratory valve and (b) an expiratory adapter.

24. The respiratory treatment apparatus of claim 13 wherein the discrete compartment is segregated from other operational components of the respiratory treatment apparatus.

25. The respiratory treatment apparatus of claim 13 wherein the chassis is arranged with one or more dividers or walls to create the discrete compartment.

26. The respiratory treatment apparatus of claim 13 further comprising an external access hatch for the discrete compartment.

27. The respiratory treatment apparatus of claim 13 wherein the expired gas inlet port of the gas routing module is configured to extend from the discrete compartment to outside of an external housing of the respiratory treatment apparatus.

* * * * *